United States Patent [19]

Middleman et al.

[11] Patent Number: 5,509,923
[45] Date of Patent: Apr. 23, 1996

[54] DEVICE FOR DISSECTING, GRASPING, OR CUTTING AN OBJECT

[75] Inventors: Lee M. Middleman, Portola Valley; Walter R. Pyka, Redwood City, both of Calif.

[73] Assignee: Raychem Corporation, Menlo Park, Calif.

[21] Appl. No.: 631,809

[22] Filed: Dec. 21, 1990

Related U.S. Application Data

[63] Continuation-in-part of Ser. No. 594,770, Oct. 9, 1990, abandoned, which is a continuation-in-part of Ser. No. 394,463, Aug. 16, 1989, abandoned.

[51] Int. Cl.$^6$ .................................................. A61B 17/00
[52] U.S. Cl. ............................. 606/207; 606/170
[58] Field of Search ............................ 604/22, 104, 105; 128/751; 606/110–114, 127, 128, 137, 159, 160, 167, 170, 174, 180, 198; 30/237, 253

[56] References Cited

U.S. PATENT DOCUMENTS

| | | |
|---|---|---|
| 1,829,559 | 10/1931 | Gilliam . |
| 2,054,149 | 9/1936 | Wappler .................................. 606/113 |
| 3,736,941 | 6/1973 | Molins et al. . |
| 4,198,960 | 4/1980 | Utsugi ..................................... 606/127 |
| 4,273,128 | 6/1981 | Lary . |
| 4,427,000 | 1/1984 | Ueda . |
| 4,467,802 | 8/1984 | Maslanka ............................... 606/127 |
| 4,505,767 | 3/1985 | Quin . |
| 4,509,517 | 4/1985 | Zibelin . |
| 4,590,938 | 5/1986 | Segura et al. .......................... 606/127 |
| 4,616,656 | 10/1986 | Nicholson et al. . |
| 4,655,219 | 4/1987 | Petrizzi . |
| 4,665,906 | 5/1987 | Jervis . |
| 4,899,743 | 2/1990 | Nicholson et al. . |
| 4,935,068 | 6/1990 | Duerig . |
| 5,064,428 | 11/1991 | Cope et al. ............................. 606/127 |
| 5,133,727 | 7/1992 | Bales et al. . |
| 5,171,233 | 12/1992 | Amplatz et al. . |

OTHER PUBLICATIONS

Hodgson, D E, *Using Shape Memory Alloys*, Shape Memory Applications, Inc. Cupertino, CA, 1988.
*Engineering Aspects of Shape Memory Alloys*, Duerig, Melton, Stockel and Wayman, 1990, pp. 369–393.

*Primary Examiner*—Stephen C. Pellegrino
*Assistant Examiner*—William W. Lewis
*Attorney, Agent, or Firm*—Sheri M. Novack; Herbert G. Burkard

[57] ABSTRACT

A device for dissecting, grasping and/or cutting an object has at least two elongate elements at least a portion of at least one of the elements is formed from a pseudoelastic material, preferably a pseudoelastic shape memory alloy. End portions of the elements can be moved away from one another and then toward one another to dissect, grasp and/or cut an object with the elements. In certain embodiments, the device further comprises an actuating means and at least a portion of the elements and/or the actuating means is formed from a pseudoelastic material. The device is particularly useful in dissecting, grasping and/or cutting objects located in difficult to reach areas, for example within the body during surgery.

21 Claims, 13 Drawing Sheets

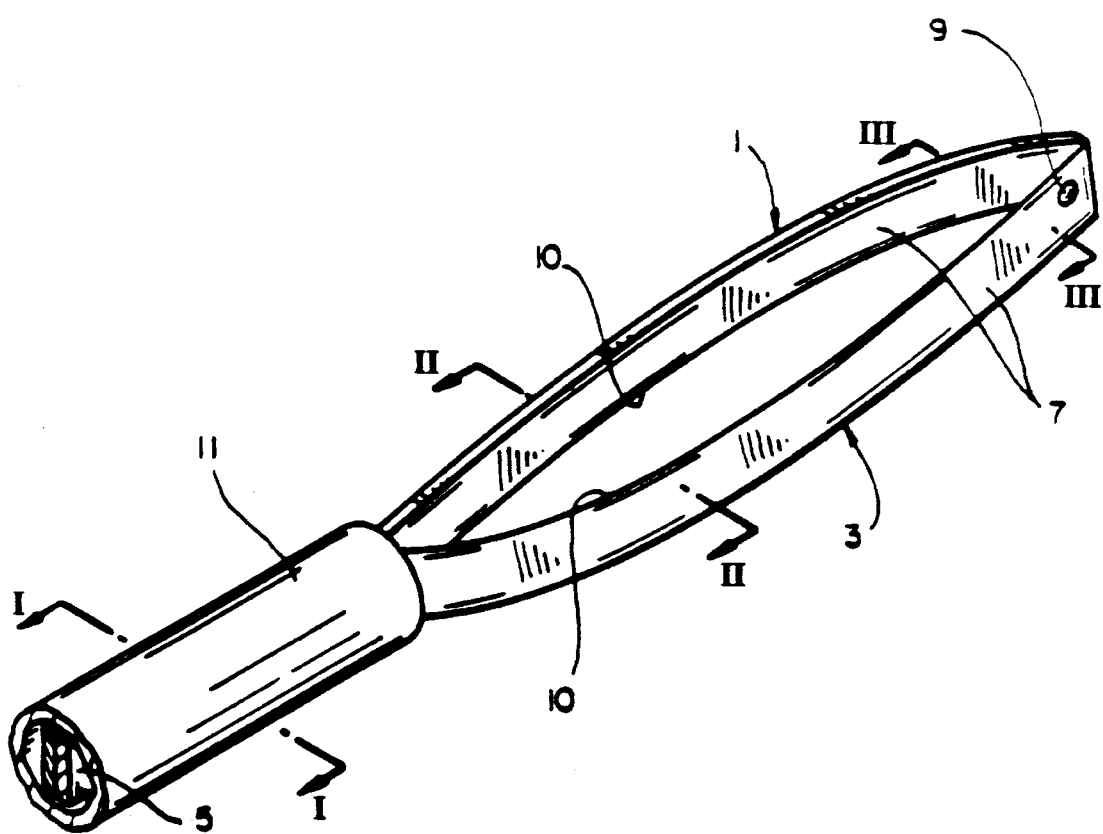
FIG_1

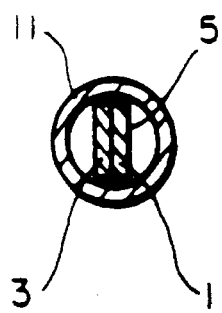
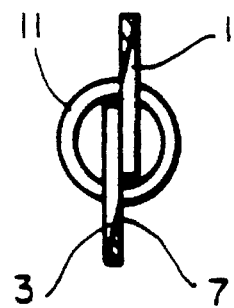
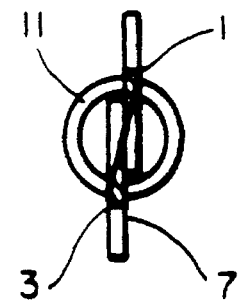
FIG_2a  FIG_2b  FIG_2c

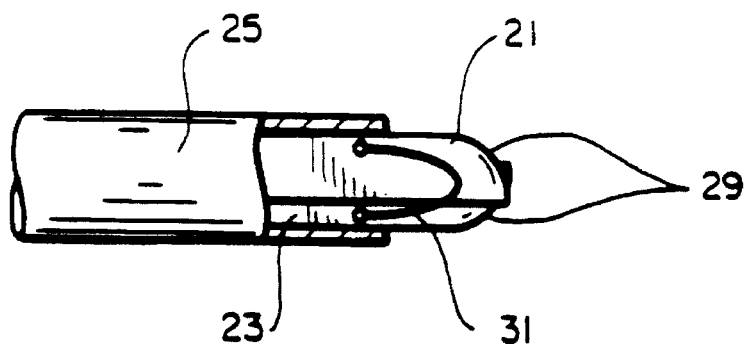
FIG_4a
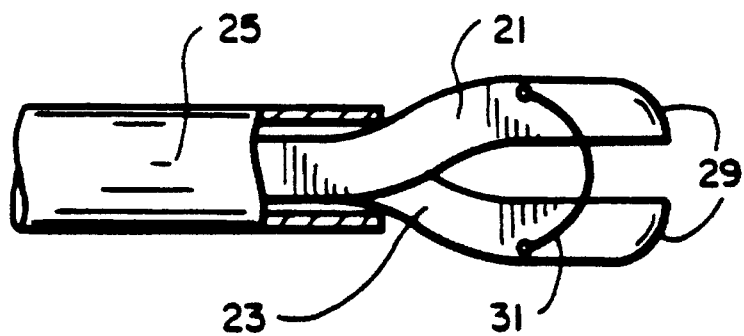
FIG_4b
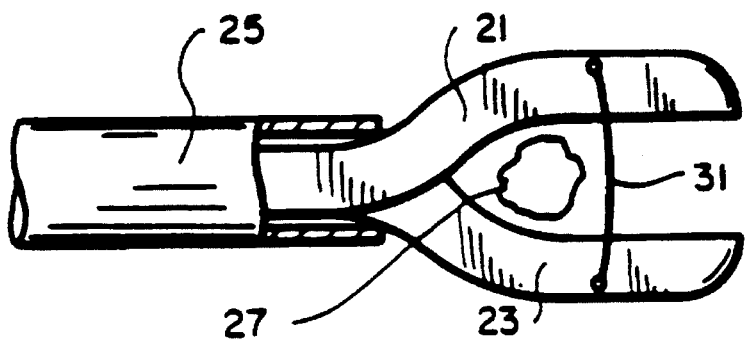
FIG_4c

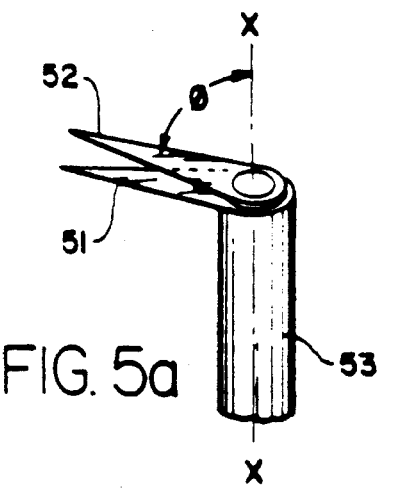
FIG. 5a
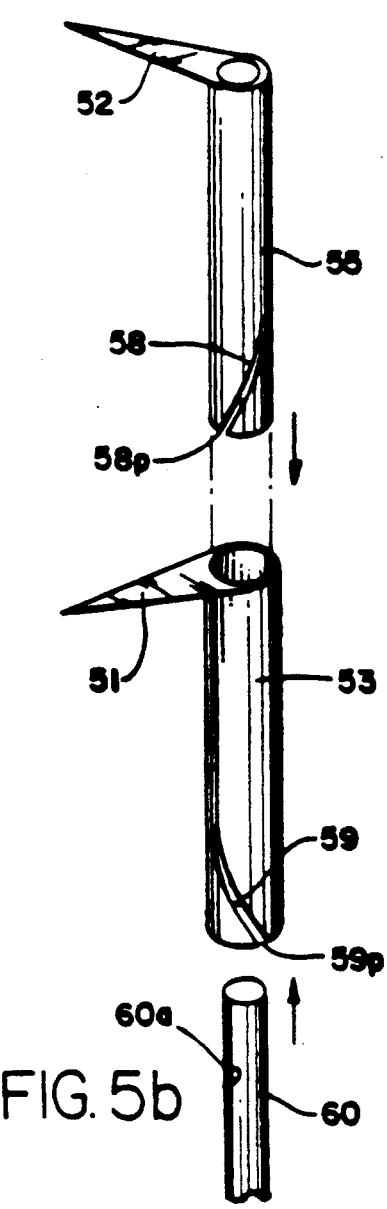
FIG. 5b
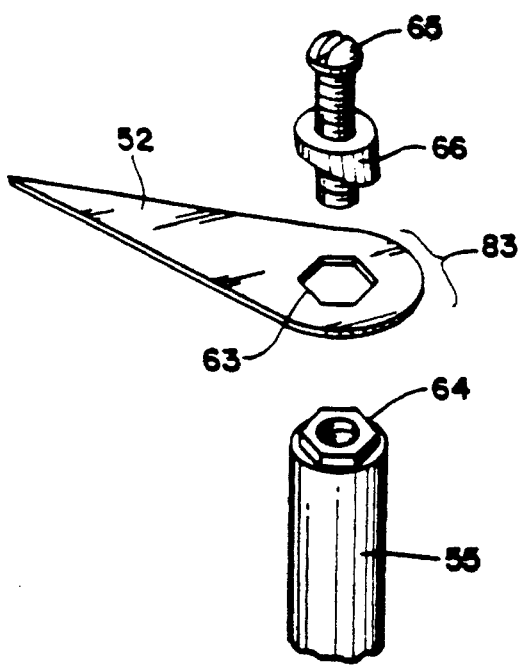
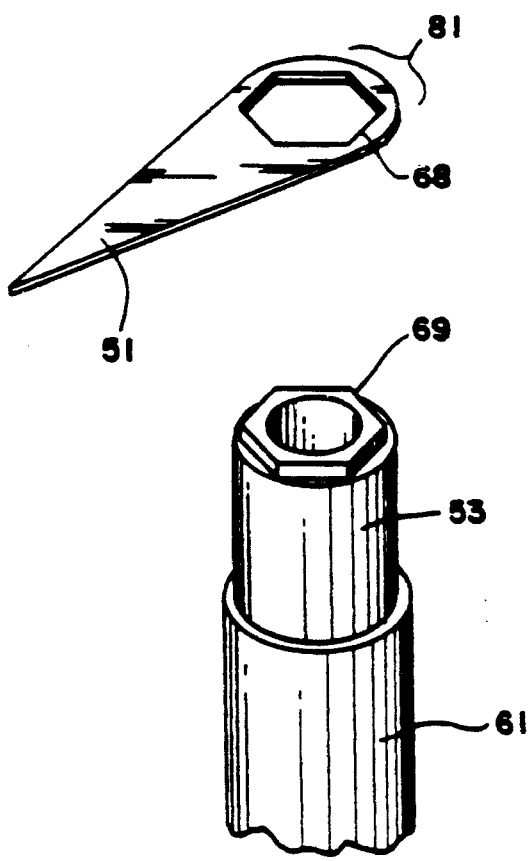
FIG. 5c 5,509,923

DEVICE FOR DISSECTING, GRASPING, OR CUTTING AN OBJECT

This application is a continuation-in-part of application Ser. No. 07/594,770, filed Oct. 9, 1990 which in turn is a continuation-in-part of application Ser. No. 07/394,463 filed Aug. 16, 1989, both abandoned the entire disclosures of each of said applications are incorporated herein by reference.

BACKGROUND OF THE INVENTION

This invention relates to a device and to a method of dissecting, grasping or cutting an object.

Many devices which are used commonly for grasping or cutting objects have two elements which can be moved towards one another and away from one another. The elements have surfaces which may be blunt or sharp so that an object positioned between them may be either grasped or cut when the elements are moved towards one another. Examples of such devices include tongs, tweezers, forceps, scissors, guillotines, and wire cutters. Such devices can also be adapted to dissect tissue, for example, by placing the elements of the device into or next to an object and then causing the elements to splay apart thereby dissecting the object.

The elements of such devices are generally rigid, and are moved relative to one another pivotally. The combined requirements that the elements be rigid and capable of pivotal movement can preclude their use in situations where there is a limited amount of space. Furthermore, it can be difficult to manipulate such devices remotely or at angles. These factors tend to make it difficult to use such devices within the body of an animal or human undergoing surgery, especially during less invasive surgical techniques, such as arthroscopy, endoscopy and laproscopy. During such surgery, it may be necessary to grasp and move tissue, for example, to expose an underlying site, to dissect tissue from surrounding tissue, and/or to cut diseased or damaged tissue.

In these less invasive surgical procedures, elongate housings have been developed to position the instrument or device into the body through a minimal incision. Example of such devices are disclosed in U.S. Pat. Nos. 2,670,519 to Recklitis, 2,114,695 to Anderson, 2,137,910 to Anderson, 3,404,677 to Springer, 3,491,747 to Robinson, 4,218,821 to Schneider, 4,423,729 to Gray, 4,612,708 to Hattori, 4,656,999 to Storz, 4,678,459 to Onik, 4,768,505 to Okada et al, European Patent No. 380,874 to Bencini and German Patents Nos. 1,266,446 to Fischer and 3,732,236 to Baumgart.

It has now been discovered that one or more elements of such grasping or cutting devices can be formed from a pseudoelastic material, preferably a pseudoelastic material, such as a shape memory alloy, which is capable of being greatly deformed without permanent deformation, to provide an improved device that can be more readily used in applications in which there is a limited amount of space. Furthermore, the device can be operated remotely or at angles more conveniently than previously used devices. The device, with appropriately configured edges can also be used to dissect tissue.

It has been proposed to make medical devices from pseudoelastic materials, but such prior art devices typically do not have elements which are splayed apart and then, preferably moved toward one another in the manner necessary in dissecting, grasping or cutting devices, such as forceps, scissors or the like. Further, prior art devices using pseudoelastic materials do not have elements which are near one another and then splay apart to separate or dissect tissue. Descriptions of medical devices made from pseudoelastic materials can be found in U.S. Pat. Nos. 4,616,656 to Nicholson et al, 4,665,906 to Jervis, 4,898,156 to Gatturna et al, 4,899,743 to Nicholson et al and 4,926,860 to Stice et al, the disclosures of which are incorporated herein by reference.

SUMMARY OF THE INVENTION

In one aspect, the present invention provides a device for dissecting an object which comprises at least two elongate elements, positioned alongside one another, each having a body portion and an end portion, the end portions of the elements:
    i being capable of being splayed apart from one another when free of transverse constraint to dissect said object from surrounding material; and
    ii being capable of being moved toward one another;
wherein a portion of at least one of the elements is formed from a pseudoelastic material.

In another aspect, the present invention provides a device for grasping or cutting an object which comprises at least two elongate elements, positioned alongside one another, each having a body portion and an end portion, the end portions of the elements:
    (i) being capable of being splayed outwardly apart from one another when free of transverse constraint and presenting grasping or cutting surfaces to an object to be grasped or cut that is placed between them; and
    (ii) being capable of being moved inwardly towards one another to grasp or cut said object;
wherein a portion of at least one of the elements is formed from a pseudoelastic material.

A further aspect of this invention comprises a device for dissecting an object which comprises
    a. at least two elongate elements, positioned alongside one another, each having a body portion and an end portion, the end portions of the elements:
      i. being capable of being splayed apart from one another when free of transverse constraint for dissecting said object from surrounding material; and
      ii. being capable of being moved toward one another; and
    b. actuating means;
wherein a portion of at least one of the elements and/or said actuating means is formed from a pseudoelastic material.

Another aspect of this invention comprises a device for grasping or cutting an object which comprises
    (a) at least two elongate elements, positioned alongside one another, each having a body portion and an end portion, the end portions of the elements:
      (i) being capable of being splayed outwardly apart from one another when free of transverse constraint and presenting grasping or cutting surfaces to an object to be grasped or cut that is placed between them; and
      (ii) being capable of being moved inwardly towards one another to grasp or cut said object; and
    (b) actuating means;
wherein a portion of at least one of the elements and/or said actuating means is formed from a pseudoelastic material.

A further aspect of this invention comprises a device for dissecting an object which comprises
    a. a hollow elongate component; and
    b. at least two elongate elements, at least part of which are positioned within said component, said elements being positioned alongside one another, each having a body portion and an end portion, the end portions of the elements:
  i. being capable of being splayed apart from one another when free of transverse constraint; and
  ii. being capable of being moved toward one another;
wherein the elements and the component are longitudinally slideable relative to one another so that at least the end portions of the elements can be slid into and out of said component and wherein a portion of at least one of the elements is formed from a pseudoelastic material.

Yet another aspect of this invention comprises a device for grasping or cutting an object which comprises
  (a) a hollow elongate component;
  (a) at least two elongate elements, at least part of which are positioned within said component, said elements being positioned alongside one another, each having a body portion and an end portion, the end portions of the elements:
    (i) being capable of being splayed outwardly apart from one another when free of transverse constraint and presenting grasping or cutting surfaces to an object to be grasped or cut that is placed between them; and
    (ii) being capable of being moved inwardly towards one another to grasp or cut said object;
wherein the elements and the component are longitudinally slideable relative to one another so that at least the end portions of the elements can be slid into and out of said component and wherein a portion of at least one of the elements is formed from a pseudoelastic material which can be deformed when under an applied stress.

A still further aspect of this invention comprises a method of dissecting an object from surrounding material, which comprises:
A. providing a device which comprises at least two elongate elements, positioned alongside one another, each having a body portion and an end portion, the end portions of the elements being capable of being splayed apart from one another when free of transverse constraint to dissect said object from surrounding material; and wherein a portion of at least one of the elements is formed from a pseudoelastic material;
B. positioning end portions adjacent the object; and
C. causing said end portions to splay apart so as to dissect said object from surrounding material.

A further aspect of this invention comprises a method of grasping or cutting an object, which comprises:
  i. providing any one of the cutting or grasping devices as described above;
  ii. positioning the object between splayed apart end portions of the elements; and
  iii. causing said end portions to move toward one another so as to grasp or cut said object.

The pseudoelastic material is preferably a shape memory alloy, such as a nickel/titanium-based alloy, as discussed more fully below.

BRIEF DESCRIPTION OF THE DRAWINGS

The invention will be better understood with reference to the accompanying drawings, in which:

FIG. 1 is an isometric view of a device of the invention;

FIGS. 2 (a) to (c) are cross-sections through the device shown in FIG. 1, taken at lines A—A, B—B and C—C respectively;

FIGS. 4 (a) to (c) are elevational views, partially in section, of another embodiment of the device at various stages during a cutting or grasping operation.

DETAILED DESCRIPTION OF THE INVENTION

Figure 3:
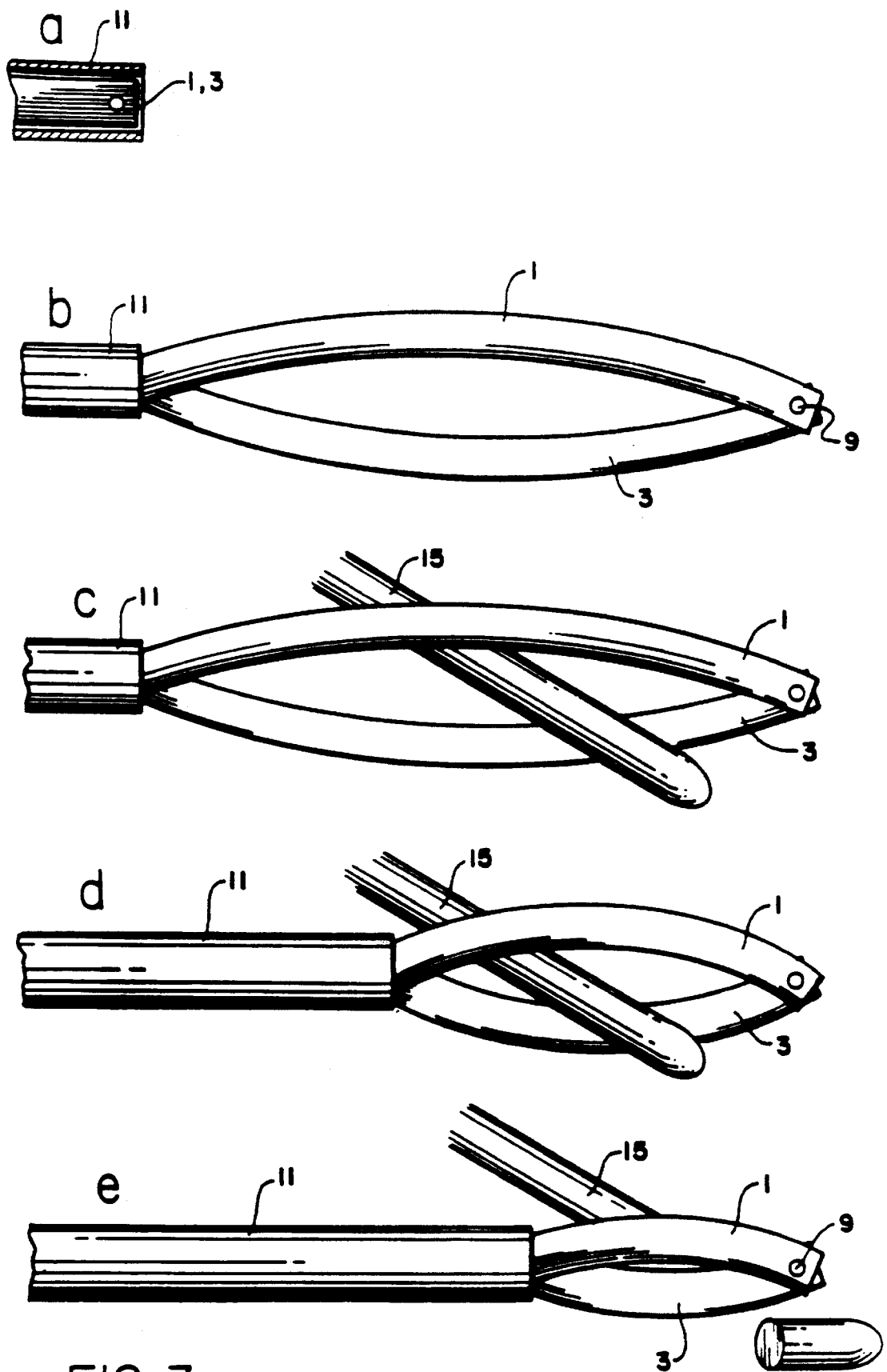
FIGS. 3 (a) to (e) are elevational views of a first embodiment of the device shown in FIG. 1 at various stages during a cutting operation.

The device of this invention comprises a hollow elongate component and two elongate elements. Preferably, the hollow component is tubular. This has the advantage that the device can be operated remotely.

The material of the hollow component may be polymeric. It may be flexible or rigid. If made of polymeric material, the material may be reinforced, for example, with fibers, to enable it to withstand the forces exerted on it by the elements while they are constrained within and deformed by the component. A suitable polymeric material for the component is, for example, polytetrafluoroethylene, reinforced with braided fibers. Alternatively, the material of the hollow component may be metallic, for example stainless steel. A preferred hollow component is an elongate tube, preferably formed from stainless steel. The elongate hollow component can be, for example, a tubular housing, cannula, catheter or sheath.

The hollow component may be circular in cross-section which can have the advantage that it permits deformation of the elements substantially uniformly in all directions. Other cross-sections may be preferable in some situations. For example, it can be advantageous to use a hollow component which has the same shape in cross-section as the elements which are received within it, to minimize twisting of the elements relative to one another.

Preferably, the elements are at least partially formed from a pseudoelastic material, such as a shape memory alloy that exhibits pseudoelasticity. Shape memory alloys which exhibit superelasticity (also referred in the literature as non-linear pseudoelasticity), are especially preferred. As a superelastic shape memory alloy is increasingly deformed from its unconstrained shape, some of its austenitic phase changes into stress-induced-martensite. The stress/strain curve presents a plateau during this phase change. This means that while the alloy undergoes this phase change, it can deform greatly with only minimal increases in loading. Therefore, cutting, dissecting and grasping elements comprising superelastic shape memory alloys have a built-in safety feature. These elements can be designed (using appropriately treated alloys and appropriate dimensions) such that when they are loaded beyond a certain amount, the elements will tend to deform with a concomitant austenite to stress-induced-martensite phase change, instead of merely presenting a greater resistance with limited deformation to the load, which is seen with conventional metals.

U.S. Pat. No. 4,935,068, of Duerig which is commonly assigned with the present application and incorporated herein by reference, teaches the fundamental principles of shape memory alloys. Some alloys which are capable of transforming between martensitic and austenitic phases are able to exhibit a shape memory effect. The transformation between phases may be caused by a change in temperature. For example, a shape memory alloy in the martensitic phase will begin to transform to the austenitic phase when its temperature rises above $A_s$ and the transformation will be complete when the temperature rises above $A_f$. The forward transformation will begin when the temperature drops below $M_s$ and will be complete when the temperature drops below $M_f$. The temperatures $M_s$, $M_f$, $A_s$, and $A_f$ define the thermal transformation hysteresis loop of the shape memory alloy.

Under certain conditions, shape memory alloys exhibit pseudoelasticity, which does not rely on temperature change in order to accomplish shape change. A pseudoelastic alloy is capable of being elastically deformed far beyond the elastic limits of conventional metals.

The property of pseudoelasticity of certain shape memory alloys, which preferably is used in the devices of this invention, is the subject of a paper entitled "An Engineer's Perspective of Pseudoelasticity", by T. W. Duerig and R. Zadno, published in *Engineering Aspects of Shape Memory Alloys,* page 380, T. W. Duerig, K. Melton, D. Stoeckel, and M. Wayman, editors, Butterworth Publishers, 1990 (proceedings of a conference entitled "Engineering Aspects of Shape Memory Alloys", held in Lansing, Mich. in Aug. 1988). As discussed in the paper, the disclosure of which is incorporated herein by reference, certain alloys are capable of exhibiting pseudoelasticity of two types. "Superelasticity" arises in appropriately treated alloys while they are in their austenitic phase at a temperature which is greater than $A_s$ and less than $M_d$ ($A_s$ is the temperature at which, when a shape memory alloy in its martensitic phase is heated, the transformation to the austenitic phase begins, and $M_d$ is the maximum temperature at which the transformation to the martensitic phase can be induced by the application of stress). Superelasticity can be achieved when the alloy is annealed at a temperature which is less than the temperature at which the alloy is fully recrystallized. Alternative methods of creating superelasticity in shape memory alloys, such as solution treating and aging, or alloying, are also discussed in "An Engineer's Perspective of Pseudoelasticity", referenced above. An article may be provided with a desired configuration by holding it in that configuration during annealing, or during solution treatment and aging. An article formed from an alloy which exhibits superelasticity can be deformed substantially reversibly by 11% or more. In contrast, "linear pseudoelasticity", is believed not to be accompanied by a phase change. It is exhibited by shape memory alloys which have been cold worked or irradiated to stabilize the martensite, but have not been annealed in the manner discussed above. An article formed from an alloy which exhibits linear pseudoelasticity can be deformed substantially reversibly by 4% or more. The treatment of shape memory alloys to enhance their pseudoelastic properties is also discussed in above-mentioned U.S. Pat. No. 4,935,068 to Duerig, incorporated herein by reference.

While the alloy that is used in the devices of this invention may exhibit either linear pseudoelasticity or superelasticity (which is sometimes referred to as non-linear pseudoelasticity), or pseudoelasticity of an intermediate type, it is generally preferred that it exhibit superelasticity because of the large amount of deformation that is available without the onset of plasticity. U.S. Pat. No. 4,665,906 to Jervis, which is commonly assigned with the present application and is incorporated herein by reference, teaches the use of pseudoelastic shape memory alloys in medical devices.

The pseudoelastic material will be selected according to the characteristics desired of the article. When a shape memory alloy is used, it is preferably a nickel titanium based alloy, which may include additional elements which might affect the yield strength that is available from the alloy or the temperature at which particular desired pseudoelastic characteristics are obtained. For example, the alloy may be a binary alloy consisting essentially of nickel and titanium, for example 50.8 atomic percent nickel and 49.2 atomic percent titanium, or it may include a quantity of a third element such as copper, cobalt, vanadium, chromium or iron. Alloys consisting essentially of nickel, titanium and vanadium, such as disclosed in U.S. Pat. No. 4,505,767, the disclosure of which is incorporated herein by reference, are preferred for some applications, particularly since they can also exhibit superelastic properties at or around body temperatures, and because they are stiffer and/or can store more elastic energy. Copper based alloys may also be used, for example alloys consisting essentially of copper, aluminum and nickel; copper, aluminum and zinc; and copper and zinc.

An article exhibiting superelasticity can be substantially reversibly deformed, by as much as eleven percent or more. For example, a 1.00 meter length of superelastic wire may be stretched to 1.11 meters in length, wherein its alloy will undergo a phase change to at least a partially more martensitic phase known as stress-induced-martensite. Upon release of the stress, the wire will return substantially to its 1.00 meter length, and its alloy will, correspondingly, return at least substantially toward its more austenitic phase. By way of contrast, a similar wire of spring steel or other conventional metal may only be elastically stretched approximately one percent, or to 1.01 meter in length. Any further stretching of the conventional wire, if not resulting in actual breakage of the wire, will result in a non-elastic (plastic) transformation such that, upon relief of the stress, the wire will not return to its original length. Linear pseudoelastic and superelastic materials may also be bent, twisted, and compressed, rather than stretched, to a far greater degree than conventional metals.

It is believed that the superelastic property is achieved by phase transformation within the alloy, rather than by the dislocation movements which occur during the plastic deformation of ordinary metals. A superelastic material may be deformed and released thousands of times, without being subject to breakage due to the metal fatigue which limits the number of deformation cycles which an ordinary metal may undergo without failure.

As discussed above, the device of the invention has the advantage that, by use of elongate elements formed at least partially from a pseudoelastic material which can be deformed, it can be used in applications in which there is a limited amount of space. Furthermore, the device can be operated remotely or at an angle more conveniently than many previously used devices.

In certain embodiments of the invention, at least one of the end portions of the elongate elements is formed from a pseudoelastic material, preferably a pseudoelastic shape memory alloy, and that end portion may have a curved configuration when not constrained and can be deformed into a straightened configuration when within a constraint, such as a hollow component. The term "straightened configuration" means that the configuration of the element is straighter when deformed than it is when not deformed. This may be used in dissection (the separation of tissues). When the end portion of the element (or end portions of the elements if both are of a pseudoelastic material) is extruded from the hollow component it is no longer constrained and reverts or recovers to splay away from the other element. When the end portion is withdrawn back into the hollow component, or the hollow component is drawn over the end portion, it moves toward the other end portion grasping or cutting any object placed between them.

In some embodiments of the invention, the end portions of the elongate elements are formed from a pseudoelastic material, preferably a pseudoelastic shape memory alloy, and are deformed into a straightened configuration when within the hollow component and curve at an angle to the end of the component when extended therefrom.

In certain other embodiments the end portions of the elongate elements are formed from a pseudoelastic material, preferably a pseudoelastic shape memory alloy, and are deformed into a curved configuration when within the component and are substantially straight when extruded from the component.

In still other embodiments, the body portion of one or both of the elongate elements is formed from a pseudoelastic material, preferably a pseudoelastic shape memory alloy, and the body portion of the element becomes curved on exiting the component, thereby splaying the end portion away from the other end portion.

In any embodiment, an actuating means, which may be formed from a pseudoelastic material, preferably a pseudoelastic shape memory alloy, can be provided to splay the end portions apart from one another and/or to move them toward one another. In such embodiments, it is not necessary for the elongate elements to be formed from a pseudoelastic material.

In summarizing, at least a portion of at least one, preferably each, of the elongate elements is formed from a pseudoelastic material, preferably a pseudoelastic shape memory alloy. The use of a shape memory alloy which exhibits pseudoelasticity has the advantage that the amount of elastic deformation that is available is large compared with that available from many other materials. In certain preferred embodiments, the end portion of one or both of the elements is formed from a pseudoelastic shape memory alloy. In other embodiments, a section of the body portion of one or both of the elements is formed from a pseudoelastic shape memory alloy. The large amount of elastic deformation of the elements allows the device to be used to dissect, grasp and/or cut large objects, while ensuring also that the device has a small transverse dimension when the elements are deformed inwardly, allowing the device to pass through small spaces.

The end and body portions of the elongate elements may be formed from the same material, for example, both may be formed from a shape memory alloy, for convenience. Frequently, however, it may be preferable to use different materials because of the different functions that the end and body portions might have to serve. For example, the end portions may be of stainless steel or the like to provide a sharp cutting edge or a cutting edge of stainless steel may be provided on a part of end portions formed from a sharp memory alloy. The cross-sections of the end and body portions will generally be different, although this need not necessarily be the case. For example, the end portions may be rectangular to present a grasping surface or triangular to present a cutting surface, and the body portions may be rectangular for rigidity.

In some embodiments, the end portions of the elongate elements are pivotally connected to one another towards their free ends. This minimizes the possibility of an object becoming dislocated from the device before it is grasped or cut. The device may then be used to move an object once it has been positioned between the elements. This can also be achieved when the elements are not joined together at their free ends, but with less control in some situations. When the elements are not connected directly at their free ends, they may be connected by a flexible component which extends between the end portions of the elements so as, together with the end portions of the elements, to form a closed loop. Leaving the elements unattached at their free ends can facilitate positioning the device so that the object is located between the elements. The tips of the free ends may be blunt, especially when the elements are not attached at their free ends. Alternatively, the free ends may be pointed to facilitate dissection, for example.

The end portions of the elongate elements may be provided with a cutting edge of a material other than a shape memory alloy. The cutting edge may be inlaid in the end portion or can extend from the end portion of the device.

Preferably the body portions of the elongate elements are attached to one another. This can facilitate manipulation of the two elements. For example, the elements may be attached to one another by adhesive material or by fasteners such as screws or rivets, or the elements may be formed as a single body of material. Alternatively, the elements may be attached to an elongate member by which they are moved longitudinally relative to the hollow component. For example, such a member may be hollow, at least at its end, and the elements may be received within the member.

The elongate elements may be symmetrical when they are splayed outwardly apart, and preferably also when deformed inwardly. However, for some applications, it might be appropriate for the elements not to be symmetrical, or for the elements not to be deformed symmetrically (for example only one of the elements might be deformed), or both.

The cutting surfaces of the elongate elements may abut one another in the manner of wire cutters, or they may cross one another in the manner of shears. The grasping surfaces of the elements may abut one another and be sufficiently blunt to avoid cutting the object to be grasped. Alternatively, the grasping surfaces need not be configured so as to contact each other in the manner of cutting devices. The object being grasped need merely be entrapped between the end portions of the elements. The grasping surfaces may be ridged or contain protuberances to assist in grasping the object.

In certain embodiments, an object may be grasped or cut using the device of the invention by bringing the device and the object together while the elongate elements are positioned at least partially within the component, and by then moving the hollow component and the elements longitudinally relative to one another, so that the end portions of the elements extend from the object and become splayed outwardly. This action can be used to spread or dissect surrounding material from the object, if desired, to isolate the object. The object can then be positioned between the elements to be grasped or cut in accordance with the method described above.

In other embodiments, the device is provided with means for actuating the end portions of the elongate elements, which are not necessarily formed from a pseudoelastic. Illustrative actuating means are described more fully below with reference to the drawings and include rack and pinion means, pin and slot means, four-bar linkages and the like. In certain embodiments, the actuating means may be formed of a pseudoelastic material. The actuating means may permit the elements to be rotated. The actuating means may also provide suitable means for irrigating the elements, or conduct electrical current to one or both of the elements, if desired.

The device will be particularly useful in applications in which access to an object to be dissected, cut or grasped is restricted, for example in medical applications in which the object to be dissected, cut or grasped is a part of a human or animal body. In these applications, the elongate elements may be positioned in the body by means of a hollow component in the from of a cannula, catheter or sheath introduced, for example, through an opening into a body cavity.

The device may be arranged so that the axis on which the elements dissect, cut and/or grasp the object is not coaxial with the axis of at least a significant portion of the hollow component. This may be arranged, for example, by providing the elongate elements with a suitable bend. The elements may be deformed from their bent configuration towards their straight configuration, and held in the straight configuration, by the hollow component while they are within it. Alternatively, it may be arranged by use of a hollow component which is bent towards the end from which the elements extend.

The device may also be useful in the assembly of mechanical, electrical or other equipment, for example by means of robots.

Turning now to the drawings, FIGS. 1 and 2 show a cutting or grasping device which comprises two elongate elements 1 and 3, each having a body portion 5 and an end portion 7. The end portions are joined together pivotally at their free ends by a pin 9. The end portions preferably have a triangular cross-section, where the apex of the triangle provides a cutting surface 10. Alternatively, any flat cross-sectional area may present a grasping surface. Other possible cross-sectional areas are illustrated in FIGS. 6(a) to (e).

The elongate elements are preferably formed from a pseudoelastic material, preferably a shape memory alloy which has been treated so that it exhibits pseudoelasticity in the temperature range between ambient temperature and a temperature above body temperature.

Elongate elements 1 and 3 are located within an elongate housing 11 within which they can slide longitudinally, the housing preferably being a stiff tubular sheath. The elongate elements can be extended beyond the end of housing 11 by longitudinally moving them relative to housing 11 via any suitable manually operated mechanism.

FIG. 2 shows the cross-sectional configurations of elongate elements 1 and 3 at positions A—A, B—B, and C—C of FIG. 1, which illustrates the elongate elements splayed apart.

FIG. 3 (a) shows a cutting device with elongate elements 1 and 3 restricted completely within housing 11, which holds the elongate elements in a deformed configuration inwardly towards one another. The housing is positioned as desired relative to an object to be cut (or dissected or grasped) while the elongate elements are in this configuration. Once so positioned, the end portions 7 of the elongate elements are caused to extend from the housing, by relative movement of the elements and the housing. Once released from the transverse constraint imposed by the housing, end portions 7 of the elements splay outwardly apart, as shown in FIG. 3 (b), allowing an object 15 to be positioned between them, as shown in FIG. 3 (c).

Object 15 is caused to engage the surfaces 10 of elongate elements 1 and 3. Relative longitudinal movement of the elongate elements and the housing will force at least parts of the elongate elements together, thereby grasping or cutting the object, as shown in FIGS. 3 (d) and 3 (e). If desired, object 15 can be moved by holding the housing and moving the elongate elements. If it is desired not to move object 15, the elongate elements are held fixed and the housing is moved. The elongate elements can be retracted into the housing for removal of the device from the site of the dissecting, cutting and/or cutting operation.

The end portions 7 (or any other portion, as desired) of elongate elements 1 and 3 may represent sections of spherical surfaces to facilitate the splaying and closing. End portions 7 may be used to grasp, instead of cutting, tissues. The grasping function would be facilitated if end portions 7 do not have cutting surfaces 10, and if end portions 7 are not fully retracted back into housing 11. Furthermore, the splaying action of elongate elements 1 and 3 may be utilized to separate tissues for dissection.

FIG. 4 shows a device which comprises two elongate elements 21 and 23 that are preferably formed from a pseudoelastic material and more preferably a shape memory alloy which has been treated so that it exhibits superelastic behavior. The elements can slide longitudinally within a tubular housing 25. FIG. 4 (a) shows the device with the elongate elements 21 and 23 positioned almost entirely within the tubular housing 25. Housing 25 constrains elongate elements 21 and 23 in straightened and deformed shapes.

As elongate elements 21 and 23 are moved longitudinally relative to housing 25, the elongate elements extend from the end of housing 25, as shown in FIGS. 4 (b) and 4 (c). As they extend from the end of housing 25, the elongate elements become unconstrained and recover toward their preset curved shapes pseudoelastically. They pseudoelastically splay outwardly so that they can receive an object 27 between them or, alternatively, be used to dissect surrounding material. The elongate elements may be interconnected indirectly towards their free ends 29 by a flexible component, such as a piece of wire 31, which helps to prevent dislocation of object 27 from between the elongate elements. Object 27 is cut or grasped by relative movement between housing 25 and the elongate elements, such that the elongate elements become constrained within the housing, generally as described above with reference to FIG. 3. The splaying action of elongate elements 21 and 23 may also be utilized to separate tissues for dissection. Elongate elements 21 and 23 may curve out of the plane of the paper.

Figure 5D:
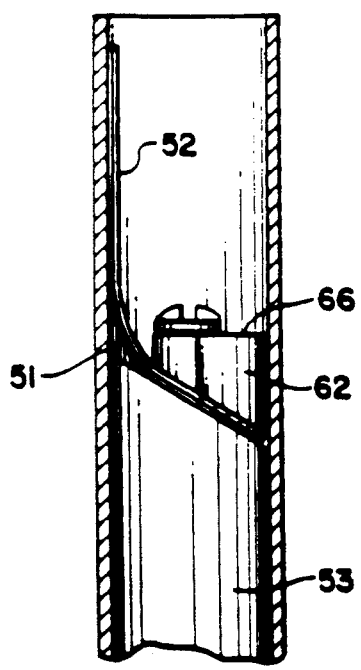
FIGS. 5 (a) to (e) illustrate an embodiment of a device in accordance with this invention in which the end portions and body portions of the elongate elements are integral and are moved by a rotational actuator made of a material other than a pseudoelastic material.
Figure 5E:
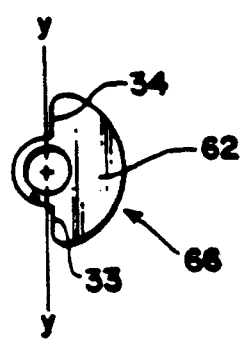
Figure 6A:
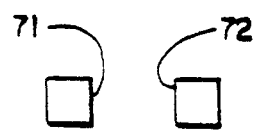
FIGS. 6 (a) to (e) illustrate representative cross sections of end portions of the elements adapted to grasp or cut an object.
Figure 6B:
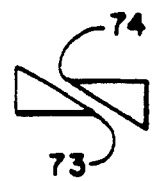
Figure 6C:
Figure 6D:
Figure 6E:
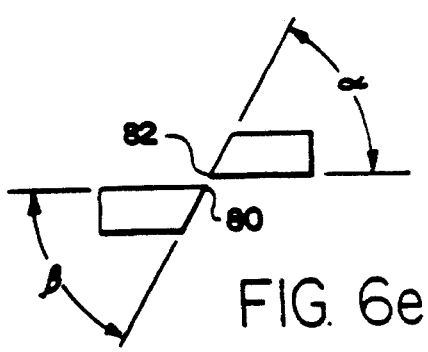
Figure 7A:
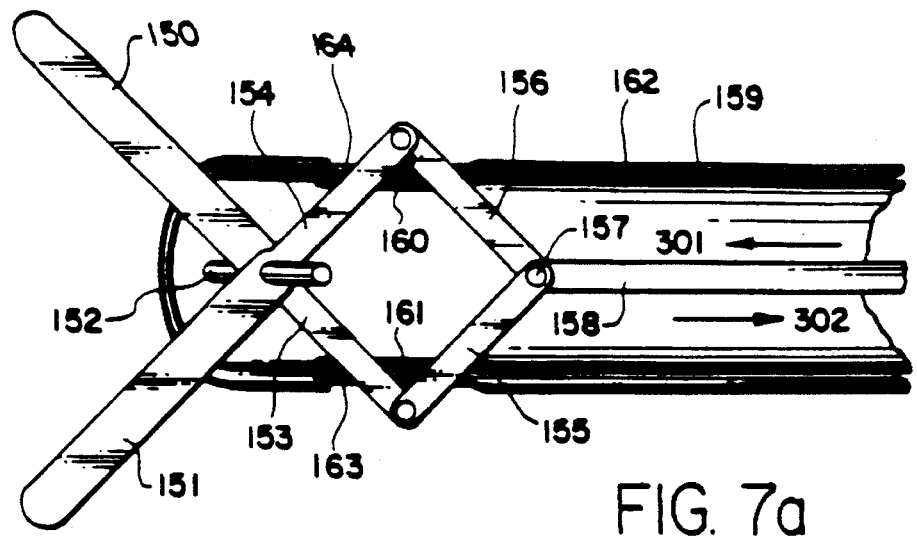
FIGS. 7 (a) to (e) illustrate various actuating means which function to cause the elements to splay apart and come together and, optionally, rotate the elements, and/or withdraw the elements into or out of the hollow component.
Figure 7B:
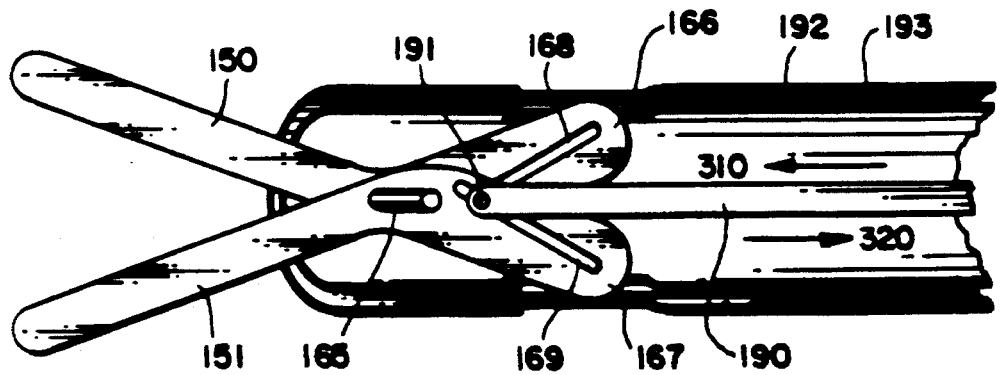
Figure 7C:
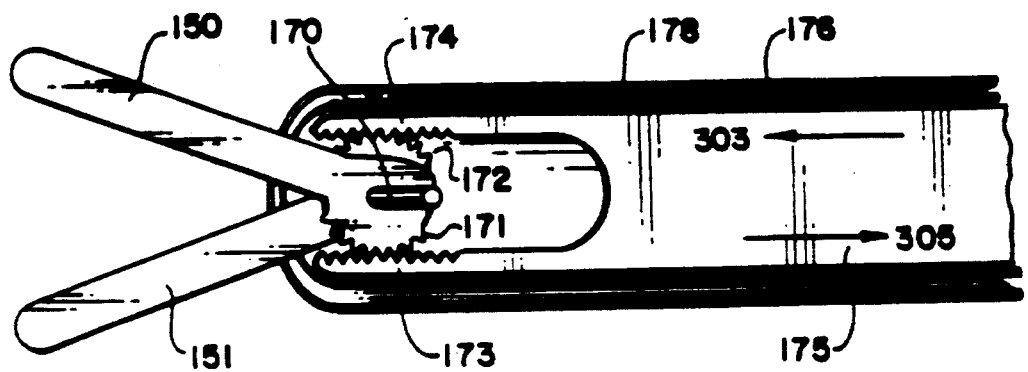
Figure 7D:
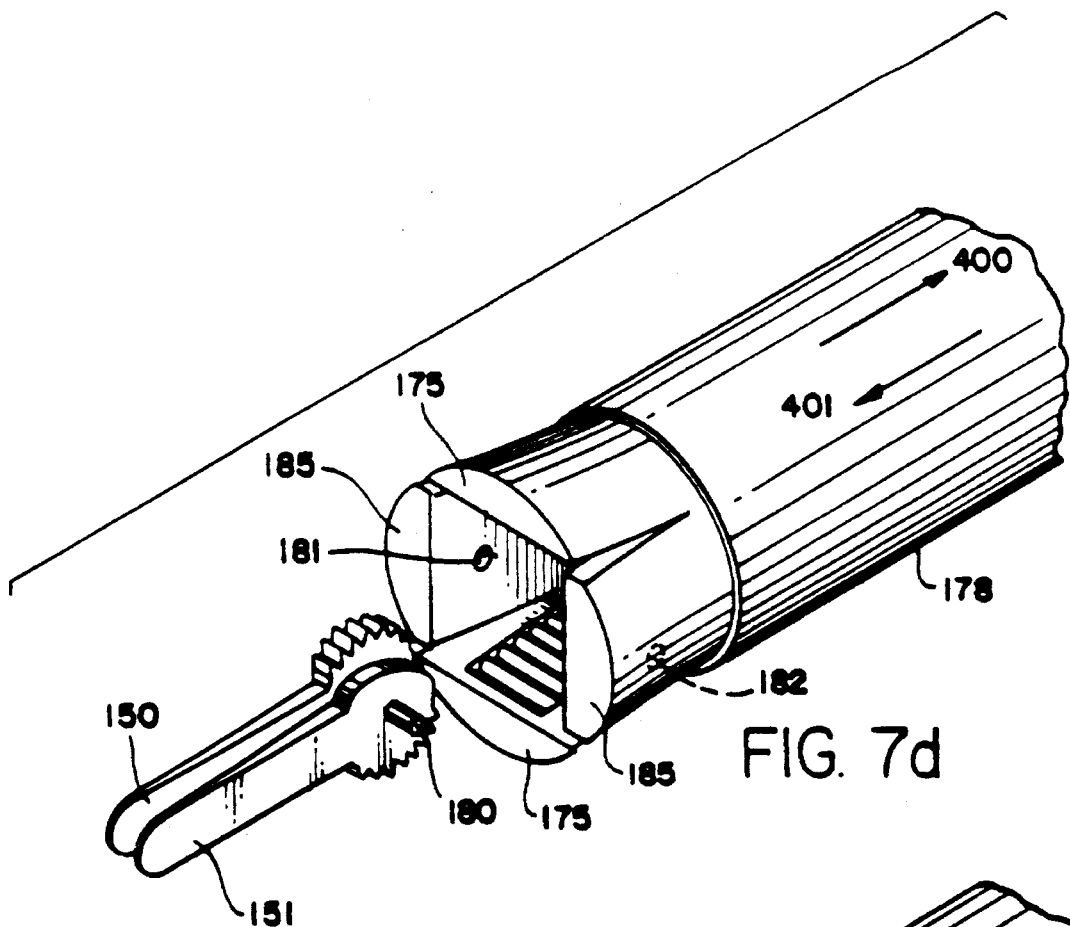
Figure 7E:
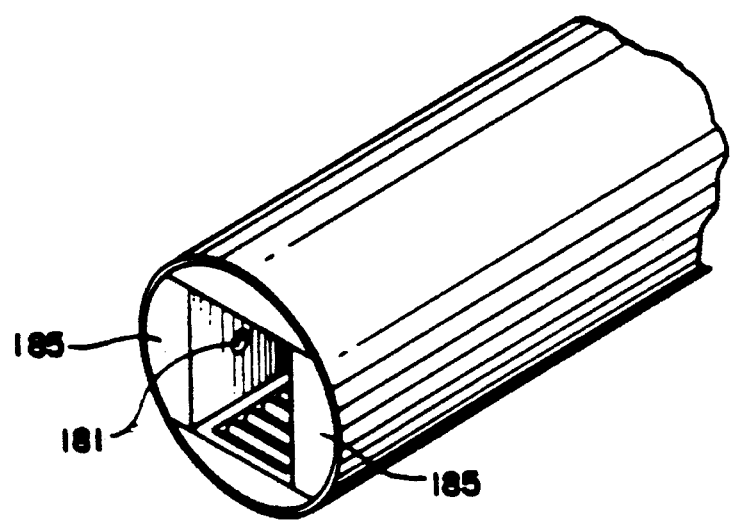

FIG. 5 (a) illustrates an embodiment of the invention in which elongate elements 51 and 52 are substantially planar and straight in their unconstrained shapes, but are located in a plane which deviates by an angle ø from a plane which includes the axis x—x of a hollow tube 53. In this embodiment, elongate elements 51 and 52 are attached to outer tube 53 and inner tube 55, respectively, as shown in FIG. 5 (b). The proximal end (i.e., the end opposite the elongate element 52) of inner tube 55 is provided with a groove 58, and inner tube 55 is positioned within outer tube 53. The proximal end of outer tube 53 is provided with a groove 59, which extends in a direction opposite to groove 58 of inner tube 55. Plunger 60 is provided with a peg 60a. The plunger may be positioned at the proximal end of the tubes. The proximal ends 58p and 59p of grooves 58 and 59, respectively, are positioned such that they overlap and are engaged by peg 60a. When peg 60a engages proximal ends 58p and 59p of grooves 58 and 59, elongate elements 51 and 52 are preferably splayed apart in the plane defined by their respective flat surfaces. When plunger 60 is pushed into inner tube 55 in a distal direction toward the elongate elements, peg 60a engages grooves 58 and 59, causing tubes 53 and 55, and thereby the elongate elements 51 and 52, to rotate in opposite directions. Preferentially, this rotation would cause the elongate elements to rotate into a more overlapped configuration. The elongate elements can thereby grasp an object placed between them. If the elongate elements have cutting edges, they could thereby cut an object placed between them. When plunger 60 is withdrawn from inner tube 55 again, peg 60a could cause tubes 53 and 55 to rotate such that elongate elements 51 and 52 splay apart from their overlapped configuration. Elongate elements 51 and 52 could thereby be used to separate tissues for dissection.

With respect to this embodiment, it should be noted that the angle ø between elongate elements 51 and 52 and tubes 53 and 55 can be any number of degrees desired. In addition, the elongate elements may be curved, not only within the plane generally described by their plane of motion, but also out of the plane generally described by their plane of motion. Furthermore, there may be more than one peg on plunger 60. Correspondingly there would be additional grooves (or slots) in tubes 53 and 55. The grooves may be spiralled, and longer, such that elongate elements 51 and 52 could be caused to rotate in both directions of their overlapped position in one stroke of plunger 60. The grooves may also be located anywhere along the lengths of tubes 53 and 55. Consequently, peg 60a may be appropriately located anywhere along plunger 60. Finally, grooves 58 and 59 could be made configured such that elongate elements 51 and 52 could be brought to their overlapped configuration by withdrawing plunger 60 in a proximal direction away from the elongate elements.

FIG. 5 (c) shows one method of the attachment of elongate elements 51 and 52 onto inner and outer tubes 53 and 55, respectively. Elongate element 52 is provided with aperture 63 which fits over stem 64, which is integral with or is secured to the distal end of inner tube 55. The length of stem 64 is equal to or less than the thickness of elongate element 52. The cross-sectional shapes of aperture 63 and stem 64 are preferably noncircular, and they may, for example, be square, serrated, notched, etc. Screw 65 and washer 66 fasten elongate element 52 to inner tube 55. Washer 66 may have a beveled side to accommodate the angle ø between the axis x—x of inner tube 55 (and tube 53) and the plane of elongate elements 51 and 52 as shown in FIG. 5(c). The distal face of tube 55 and the distal face of stem 64 should also be slanted (not shown) at ø relative to the axis x—x of tube 55.

Elongate element 51 is provided with an aperture 68 which fits over stem 69, which is integral with or is secured to the distal end of outer tube 53. The length of stem 69 is preferably slightly greater than the thickness of elongate element 51, so that rotation of elongate element 51 relative to elongate element 52 is not hindered. The cross-sectional shapes of aperture 68 and stem 69 are preferably noncircular, and they may, for example, be square, serrated, notched, etc. The distal face of tube 53 and the distal face of stem 69 should be slanted (not shown) at an angle ø relative to the axis x—x of tube 53.

Inner tube 55, with attached elongate element 52, fits into outer tube 53. Elongate element 51 will be captured between the base of stem 69 and elongate element 52. Outer tube 53, with inner tube 55 contained therein, and elongate elements 51 and 52 attached, can be inserted into a sheath 61. As shown in FIG. 5 (d), when elongate elements 51 and 52 are drawn into sheath 61 (shown in cross-section), they will be deformed in a direction more parallel to axis x—x. This deformation will be facilitated if elongate elements 51 and 52 are transversely curved along their longitudinal dimensions (i.e., trough shaped). Also, if the outer diameter of tube 53 is only slightly smaller than the inner diameter of sheath 61, the circumferences of elongate elements 51 and 52 along portions 81 and 83 (i.e., the circumferences of elongate elements 51 and 52 around their respective apertures 68 and 63, except for their longitudinally extended portions), should preferably not extend beyond the outer diameter of outer tube 53. When outer tube 53 is extended distally beyond the end of sheath 61, elongate elements 51 and 52 will no longer be constrained, and they will elastically recover their preset shapes again. This deformation and shape recovery is enhanced if the elongate elements are made of a pseudoelastic shape memory alloy.

FIG. 5 (e) is a bottom view of a possible embodiment of washer 66. Projection 62 has an outer diameter which is equal to or smaller than the outer diameter of outer tube 53. The surface of projection 62, which holds elongate element 52, may be rough, or it may even have teeth or protrusions, in order to obtain a better grip on elongate element 52. Projection 62 preferably encompasses less than half of the circumferential arc of washer 66. The remaining circumference of washer 66 has a outer diameter which is equal to or smaller than the maximum diameter of the head of screw 65. The head of screw 65 preferably has a diameter which is equal to or less than the smallest diametral dimension of stem 64. As shown in FIG. 5 (d), projection 62 covers the back end of elongate element 52. In this manner, elongate element 52, and secondarily, elongate element 51, can be given as much bending length as possible when they are both constrained within sheath 61. The sides 33 and 34 of projection 62 are preferably parallel to axis y—y, where axis y—y is perpendicular to the longitudinal dimension of elongate element 52 and is perpendicular to the axis of symmetry of washer 66. This will permit ready bending of elongate element 52 along a zone which is perpendicular to its longitudinal dimension.

There may be any suitable means between outer tube 53 and inner tube 55 to prevent plunger 60 from pushing inner tube 55 out of outer 53 tube when plunger 60 is pushed in a distal direction in inner tube 55. In addition, there may be any suitable means between outer tube 53 and sheath 61, so that outer tube 53 can not be completely pushed out of sheath 61 once elongate elements 51 and 52 are adequately extended out of sheath 61 and plunger 60 is used to cause rotation of elongate elements 51 and 52. Plunger 60 can be pushed relative to sheath 61 and tubes 53 and 55 by any suitable manually operated mechanism. Examples of manually operated mechanisms include sliders, pistol grip handles, scissors handles, and syringe-plunger arrangements.

An alternate version of the embodiment of FIG. 5 would have a stiff central rod slid along an inner longitudinal bore in the plunger. In this case, the elongate elements would be attached to their respective tubes along one side of the wall of each tube, e.g. by welding or by longitudinally slitting the walls instead of being held by a screw. The central rod could then be used to straighten the elongate elements (assuming the elongate elements do not have any apertures) and deform them to be more in line with the axis of the tubes.

While most of the specific embodiments are directed to cutting devices, it is to be understood that blunt edges can replace the cutting edges in any of the embodiments. Illustrative blunt and cutting edges are shown in FIGS. 6 (a), (b), (c), (d), and (e). The cutting and grasping edges may be integral with the elements or may be formed separately and/or of different materials and attached thereto. FIG. 6 (a) illustrates grasping surfaces 71 and 72. Surfaces 71 and 72 may be flat or they may contain ridges, protrusions or the like to aid in gripping an object. FIG. 6 (b) illustrates shearing cutting edges 73 and 74 which cut an object by a shearing action. FIG. 6 (c) illustrates another pair of edges for cutting. In FIG. 6 (c), surface 75 is flat, while edge 76 provides a sharp edge for cutting an object. FIG. 6 (d) illustrates cutting edges 77 and 78. Sharp edges 77 and 78 of the triangular cross-sections meet to permit cutting. FIG. 6 (e) illustrates cutting edges 80 and 82, which are at any desired angles a and β relative to the direction of opening and closing of the elongate elements. In all of these embodiments, as well as in all of the embodiments described herein, the cutting edges or gripping surfaces could be made of any material such as steel, diamond, plastic, etc., which is attached to the elongate elements.

In any of the embodiments, dissection could be performed by providing any suitable edge opposite edges 71–78 and 80 and 82 of FIGS. 6 (a)–(e).

FIGS. 7 (a), (b), and (c) illustrate several different means of actuating elongate elements. In FIG. 7 (a), the body portions of elongate elements 150 and 151 are joined together at pivot 152. Also joined at pivot 152 is one end of a linkage composed of four links 153, 154, 155, and 156, which are pivotally connected to each other. Elongate elements 150 and 151 are preferably rigidly attached to links 153 and 154, respectively. Alternatively, links 153 and 154 may merely represent extensions of elongate elements 150 and 151, respectively. Pivot 152 is preferably fixed to a cannula 159. The pivot 157 at the other end of the linkage is joined to rod 158. When rod 158 is pushed in direction 301, pivot 157 is pushed closer to pivot 152. This will cause elongate elements 150 and 151 to splay apart. Since the transverse dimension of linkage 153, 154, 155, and 156 which is perpendicular to rod 158 becomes larger as pivot 157 approaches pivot 152, slots 160 and 161 may be provided in cannula 159 to permit pivot 157 to approach closer to pivot 152 if the transverse dimension of cannula 159 is small. Rod 158 may be pushed (or pulled) relative to cannula 159 by any suitable manually operated mechanism. Examples of manually operated mechanisms include sliders, pistol grip handles, scissors handles, and syringe-plunger arrangements.

Elongate elements 150 and 151 may be constrained in deformed and straightened shapes within a sheath 162. This will permit compact and relatively atraumatic entry into a body. Rod 158 can then be pushed axially in direction 301 within sheath 162. The linkage 153, 154, 155, and 156 will partially extend through slots 160 and 161 in cannula 159, but the inner surface of sheath 162 will prevent pivot 157 from fully approaching pivot 152. Therefore, cannula 159 will be forced to move in direction 301, and elongate elements 150 and 151 will extend from the end of sheath 162 in direction 301. In their extended position, elongate elements 150 and 151 will not be constrained, and they may recover toward their preset shape, which may, for example, be curved out of the plane of the paper. Slots 163 and 164 are provided in sheath 162 to permit rod 158 to push pivot 157 fully toward pivot 152 in order to fully splay elongate elements 150 and 151 apart. Slots 163 and 164 in sheath 162 may be made to overlap slots 160 and 161 in cannula 159 by simply extending cannula 159 far enough within sheath 162, or by extending cannula 159 far enough within sheath 162 and then rotating sheath 162 relative to cannula 159 to allow the respective slots to coincide. Rod 158 may then be used to splay or increasingly overlap elongate elements 150 and 151 as desired.

Rod 158 can be moved in direction 302 so that pivot 157 is moved as far away as possible from pivot 152. This will cause elongate elements 150 and 151 to be in their most overlapped configuration. Moving rod 158 further in direction 302 relative to sheath 162 will cause cannula 159 to slide in direction 302, and will cause elements 150 and 151 to be drawn into straightened (i.e. non-curved) shapes within sheath 162. This will permit the entire assembly to be withdrawn from the body in a compact and relatively atraumatic fashion.

The passive (reference) member of the manually operated mechanism would preferably be mounted to sheath 162. In this fashion, the extension and withdrawal of elongate elements 150 and 151 from or into sheath 162 can be accomplished by utilizing an expanded stroke of the same manually operated mechanism which is used to splay or increasingly overlap elongate elements 150 and 151. In this case, a means must be provided to prevent cannula 159 from sliding beyond a certain location within sheath 162 in direction 301. Also, a means may be provided to minimize relative motion between cannula 159 and sheath 162 while the linkage is being used to repeatedly move elongate elements 150 and 151 toward their splayed or overlapped configurations. Furthermore, the manually operated mechanism would preferably permit axial rotation of the entire assembly of sheath 162 and its contents relative to the manually operated mechanism, so that elongate elements 150 and 151 can be oriented in any desired direction relative to the manually operated mechanism.

In the configuration illustrated in FIG. 7 (a), it will be noted that movement of rod 158 in direction 301 will tend to splay elongate elements 150 and 151 apart. As described above, one method of minimizing this splaying before the device is in the correct location is to create slots in specific locations of sheath 162. In an alternative method, links 156 and 155 are shorter than links 153 and 154, and pivot 157 is already positioned as close as possible to pivot 152 during placement of the device into a body. (In this configuration, links 155 and 156 would overlap links 153 and 154, respectively.) Moving rod 158 in direction 301 will then urge elongate elements 150 and 151 toward their overlapped configuration, even though the elongate elements can be extended beyond the end of sheath 162 by motion in direction 301 when the sheath is held fixed. Elongate elements 150 and 151 can then be splayed apart by moving rod 158 in direction 302. When the device is to be withdrawn from a body, rod 158 is moved further in direction 302, so that pivot 157 is as far as possible from pivot 152, where the configuration shown in FIG. 7 (a) would be an intermediate position. Elongate elements 150 and 151 will thereby be urged back toward their overlapped configuration. Moving rod 158 even further in direction 302, relative to sheath 162, will permit withdrawal of elongate elements 150 and 151 into sheath 162.

FIG. 7 (b) shows an embodiment in which elongate elements 150 and 151 have a pivot 165 and body portions 166 and 167, respectively. Body portions 166 and 167 have slots 168 and 169, respectively. A rod 190 has a peg 191 which is oriented to slideably engage slots 168 and 169. Pivot 165 is fixed to the cannula 192, and slots 168 and 169 are preferably oriented so that motion of rod 190 in direction 310 will urge elongate elements 150 and 151 toward their overlapped configuration, and motion of rod 190 in direction 320 will splay elongate elements 150 and 151 apart. However, slots 168 and 169 could be curved such that extreme motion of rod 190 in direction 320 will again bring elongate elements 150 and 151 to their overlapped configuration. Cannula 192 may be substantially the same as cannula 159 shown in FIG. 7 (a). In addition, a sheath 193, which may substantially be the same as sheath 162 shown in FIG. 7 (a), can be utilized. The function and use of the embodiment shown in FIG. 7 (b) is then substantially the same as the embodiment shown in FIG. 7 (a).

A variation of the embodiment illustrated in FIG. 7 (b) would include elongate elements in which the slots are placed distal to the pivot point between the elongate elements. (That is, the slots are located between the pivot point and the tips of the elongate elements). Body portions 166 and 167 as shown in FIG. 7 (b), and slots 160, 161, 163, and 164 as shown in FIG. 7 (a) may then not be necessary. However, the actuating rod (such as rod 190 shown in FIG. 7 (b)), would have to be designed so that it does not interfere with the pivot point between the elongate elements.

FIG. 7 (c) shows another embodiment in which the elongate elements 150 and 151 may be made to splay apart or increasingly overlap each other. Elongate elements 150 and 151 are hinged at pivot 170, which is preferably fixed to a cannula 176. Surrounding pivot 170, elongate elements 150 and 151 each have a rounded body portion with teeth along edges 171 and 172, respectively. The teeth engage the corresponding grooves located in jaws 173 and 174 of sliding member 175. The degree of splaying or overlapping of elongate elements 150 and 151 may be limited by limiting the lengths of edges 171 or 172 which are toothed. Additionally, or alternatively, the degree of splaying or overlapping of elongate elements 150 and 151 may be limited by limiting the lengths of the grooved zones in jaws 173 and 174. Sliding member 175 is moved in direction 303 or 305 by any suitable manually operated mechanism. Examples of manually operated mechanisms include sliders, pistol grip handles, scissors handles, and syringe-plunger arrangements. Elongate elements 150 and 151 are preferably moved toward their overlapped configuration when sliding member 175 is moved in direction 303 and moved toward their splayed apart configuration when sliding member 175 is moved in direction 305 (not shown). However, toothed edges 171 and 172 can be located on elongate elements 150 and 151 such that moving sliding member 175 in direction 303 moves elongate elements 150 and 151 toward their splayed configuration and moving sliding member 175 in direction 305 moves elongate elements 150 and 151 toward their overlapped configuration (not shown).

Elongate elements 150 and 151 may be constrained in straightened shapes within a sheath 178. This will permit compact and relatively atraumatic entry into a body. Sliding member 175 can then be moved in direction 303 relative to sheath 178 in order to extend elongate elements 150 and 151 from the end of the sheath. In the preferred mode, this motion will also tend to keep elongate elements 150 and 151 in their overlapped configuration without splaying these elements apart in the wrong direction. (As described above, toothed edges 171 and/or 172 and/or the jaws 173 and/or 174 can be designed to prevent splaying in the wrong direction). Elongate elements 150 and 151 can then be repeatedly moved toward their splayed configuration or their overlapped configuration by moving sliding member 175 in directions 305 or 303, respectively, and a means may be provided to minimize relative motion between cannula 176 and sheath 178 during this repetitive motion.

Elongate elements 150 and 151 can be withdrawn back inside sheath 178 by forcibly moving sliding member 175 in direction 305 relative to sheath 178. In a preferred version (not shown) the end of sheath 178 would force elongate elements 150 and 151 into their overlapped configuration, as well as forcing elongate elements 150 and 151 into straightened shapes into sheath 178 in order to permit the entire assembly to be withdrawn from a body in a compact and relatively atraumatic fashion. Alternatively, sheath 178 can be extended over elongate elements 150 and 151 to straighten these elements into sheath 178 and to permit the entire assembly to be withdrawn from a body in a compact and relatively atraumatic fashion.

If a sheath 178 is utilized, it could be mounted to the passive (reference) member of the manually operated mechanism. In this fashion, the extension and withdrawal of elongate elements 150 and 151 from or into sheath 178 can be accomplished by utilizing an expanded stroke of the same manually operated mechanism which is used to move sliding member 175 in order to splay or increasingly overlap elongate elements 150 and 151. In addition, in order to permit the elongate elements 150 and 151 to be oriented in any desired direction relative to the manually operated mechanism, this mechanism would preferably permit axial rotation of the entire assembly of sheath 178 and its contents relative to the manually operated mechanism.

When elongate elements 150 and 151 are to be removed and replaced, it would be advantageous to move cannula 176 far enough in direction 303 so that pivot 170 is beyond the end of sheath 178. Then the pivot pin can be removed, sliding member 175 can be extended in direction 303 beyond the end of cannula 176, and elongate elements 150 and 151 can be simply slid out of jaws 173 and 174 in a direction perpendicular to the longitudinal axis of sliding member 175.

FIG. 7 (d) shows how sliding member 175 could be configured around a pivot fixing member 185, which has holes 181 and 182. Elongate elements 150 and 151 are rotatably mounted on a pin 180. The ends of pin 180 can be placed into holes 181 and 182 when sheath 178 is pulled back in direction 400, since the ends of sliding member 175 and the ends of pivot fixing member 185 can gently splay apart when they are not held within sheath 178. When sheath 178 is moved back in direction 401, elongate elements 150 and 151 will be securely held when pin 180 is within sheath 178. The end of pivot fixing member 185 which has holes 181 and 182 can be fork shaped. Preferably a means is provided which minimizes motion of pivot fixing member 185 relative to sheath 178 when sliding member 175 is utilized to repeatedly move elongate elements 150 and 151 toward their splayed or overlapped configurations. FIG. 7 (e) shows the device before sheath 178 is pulled back to permit insertion of elongate elements 150 and 151. In this configuration, pin 180 is preferably longer that the dimension between the two fork ends of pivot fixing member 185, so that pin 180 is firmly locked into place.

In the embodiments described for FIGS. 7 (a), (b), (c), and (d), the elongate elements are preferably made of a pseudoelastic material, preferably a pseudoelastic shape memory alloy. The unconstrained shapes may be curved in directions away from the general planes of the body portions of the elongate elements (e.g. out of the plane of the paper). Also, in any of the embodiments described for FIGS. 7 (a), (b), (c), and (d), the elongate elements can be used for cutting, grasping, and/or dissecting tissues. The end portions of the elongate elements can be fashioned appropriately for any of these functions, or separate appropriately designed parts may be attached to the end portions of the elongate elements.

Figure 8:
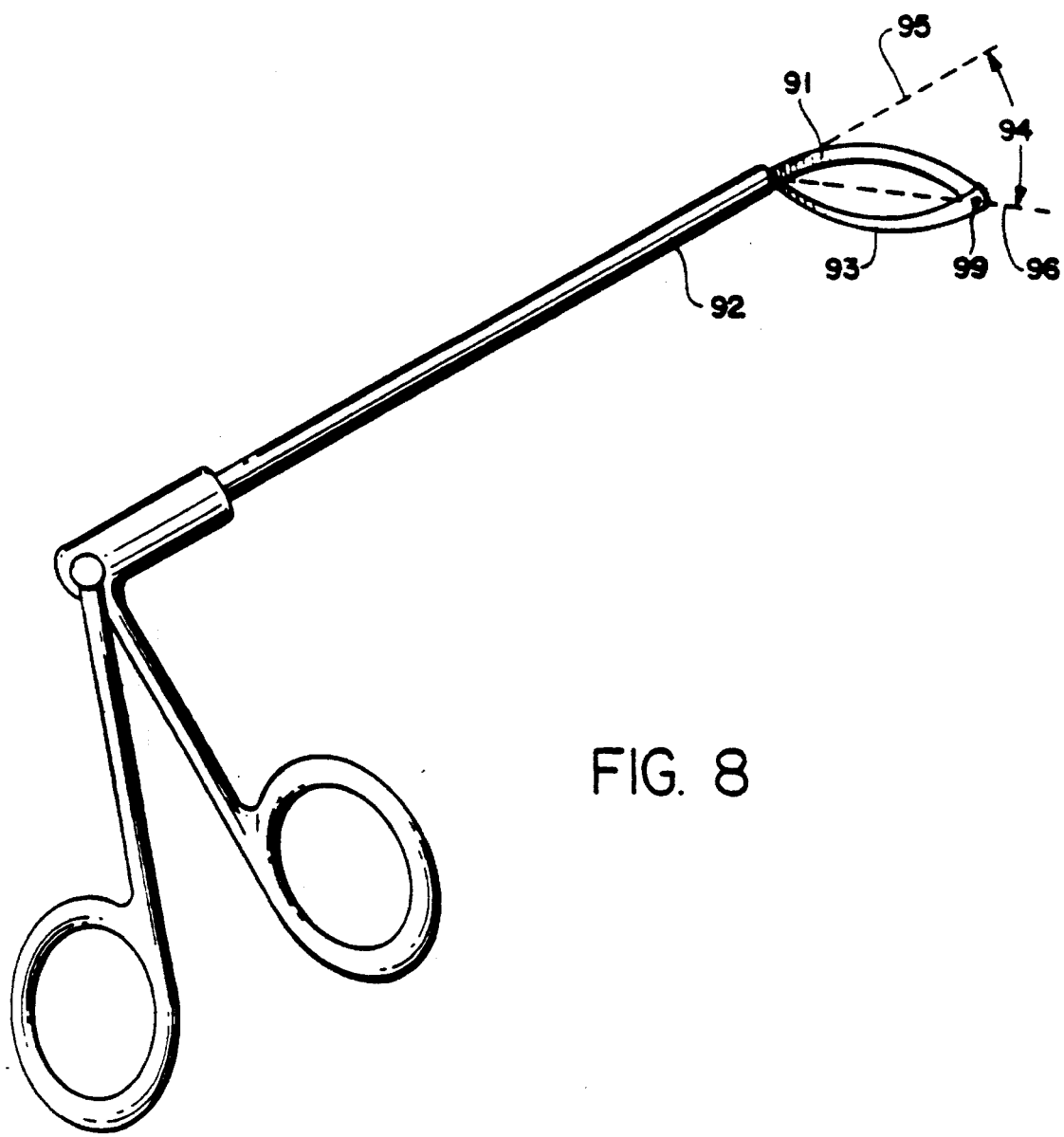
FIG. 8 illustrates an embodiment of the device of this invention in which the end portions are curved when at least partially unconstrained and pinned together pivotally at their tips.

FIG. 8 shows a cutting device, similar to the device shown in FIG. 1, with curved elongate elements 91 and 93 extended from a housing 92. This permits the elongate elements to be both open for dissecting, cutting and/or grasping and curved at an angle 94 away from axis 95 of housing 92. Angle 94 is defined by the axis 95 of housing 92 and the straight line 96 which passes through the point of intersection of axis 95 with the distal end of housing 92 and the pin 99. Angle 94 can be any desired angle, even greater than 90 degrees, thus permitting dissecting, cutting and/or grasping in a direction off axis 95. This provides access to difficult to reach locations in the body. Elongate elements 91 and 93 are preferably shaped so that they circumscribe spherical arcs which allow the elements to engage each other and perform the cutting or grasping function, either as they are retracted back into housing 92, or as housing 92 is extended over the elongate elements. The portions of elongate elements 91 and 93 which enter housing 92 assume a less curved shape. Elements 91 and 93 may be formed of a pseudoelastic material, preferably a pseudoelastic shape memory alloy.

Figure 9:
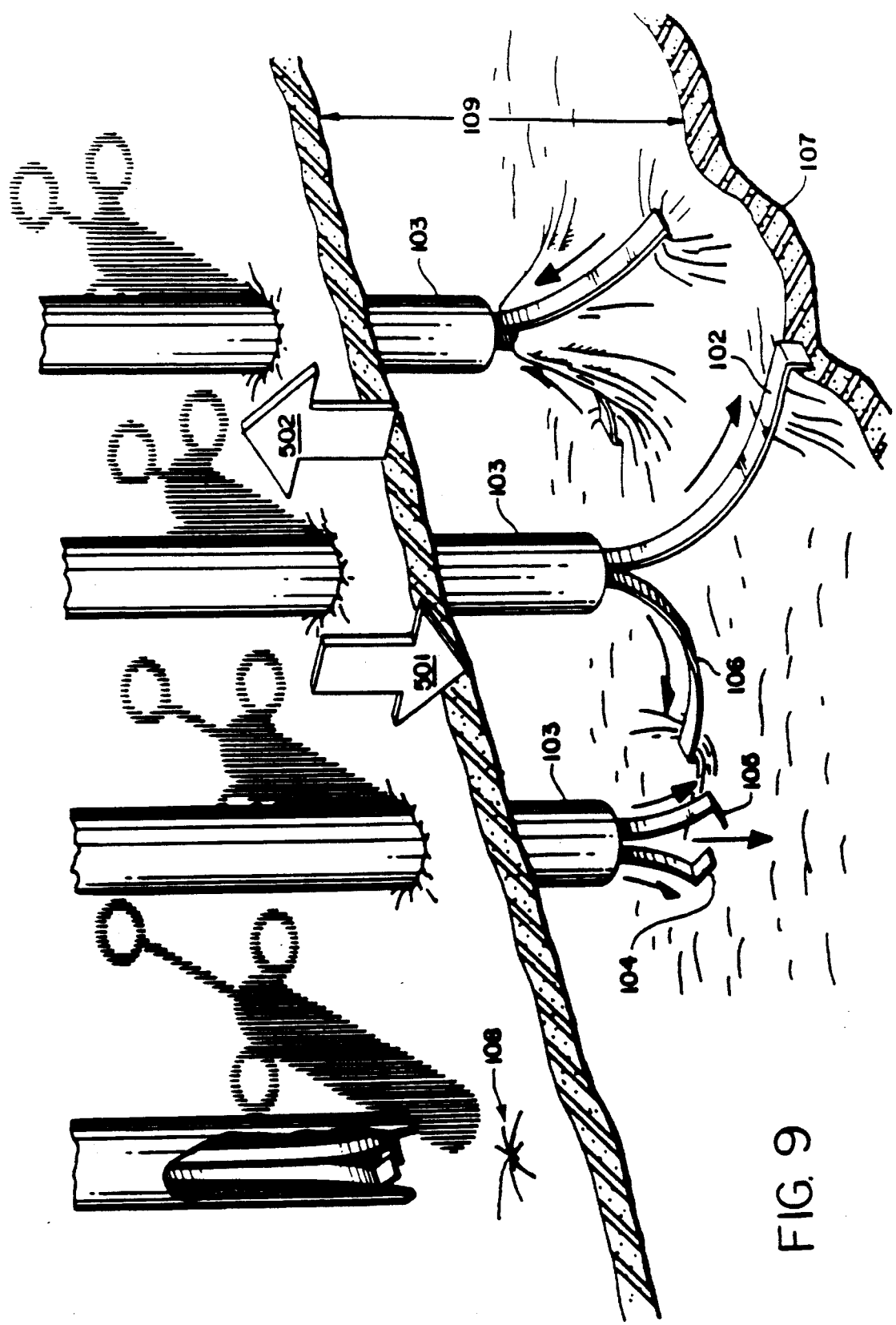
FIG. 9 demonstrates a method of using a grasping device of this invention.

FIG. 9 shows a device in which elongate elements 102 and 106, preferably made of a pseudoelastic material and more preferably a superelastic shape memory alloy, are first held constrained in straightened and deformed shapes inside a cannula 103. This permits compact placement into a body through tissue incision or orifice 108. Elongate elements 102 and 106 are then extended out of cannula 103 by moving elongate elements 102 and 106 in direction 501 relative to cannula 103. Since at least part of extended elongate elements 102 and 106 are no longer constrained, they will splay apart due to recovery of the pseudoelastic material into its preset curved unconstrained shape. Cannula 103 can be then be extended onto elongate elements 102 and 106 to force these elements to approach each other. Alternatively, elongate elements 102 and 106 can be withdrawn back into cannula 103 to force these elements to approach each other. In either mode, the tips of elongate elements 102 and 106 can be used to grasp tissue 107 or an object. The grasping function of elongate elements 102 and 106 can be enhanced by providing the end portions of these elements with bends 104 and 105, teeth (not shown), or the like at their tips. Elongate elements 102 and 106 may also be ribbed or toothed along their entire lengths (not shown). The described mode of action may permit the instrument to be used multiple times in each location.

In embodiments of the invention in which the elongate elements are made of a pseudoelastic shape memory alloy, the large pseudoelastic deformation (up to 11% or more) permits much wider splaying of elongate elements 102 and 106 over a much shorter distance 109 than would be possible with conventional metals. This permits working in more confined spaces, particularly in endoscopic or laparoscopic surgery. A variation of this embodiment may include more than two elongate elements.

Shape memory alloys have a special feature which is beneficial for any of the embodiments of this invention, but in particular for any of the embodiments in which a grasping action is desired (especially in the embodiment shown in FIG. 9). As a superelastic shape memory alloy is increasingly deformed from its unloaded shape, some of its austenitic phase changes into stress-induced-martensite. The stress strain curve presents a plateau during this phase change. This means that while the alloy undergoes this phase change, it can deform greatly with only minimal increases in loading. Therefore, elongate elements comprising superelastic shape memory alloys have a built-in safety feature. These elements can be designed (using appropriately treated alloys and appropriate dimensions) such that when they are loaded beyond a certain amount, the elements will tend to deform with a concommitant austenite to stress-induced-martensite phase change, instead of merely presenting a greater resistance with limited deformation to the load, which is seen with conventional metals.

Just as the stress strain curves of shape memory alloys present a plateau upon loading, they also present a plateau in the stress strain curve upon unloading. Unloading occurs when an elongate element made of superelastic shape memory alloy is permitted to revert from a significantly deformed shape toward its original unstressed shape. Because of the plateau, such an element can maintain an almost constant force during much of the unloading cycle until just before it is completely unloaded. This feature is especially useful for any grasper embodiment of this invention, because it means that an object held between one or more elongate elements made of a superelastic shape memory alloy can be gripped with nearly a constant force despite decreases in the amount(s) of deformation of the element(s).

Figure 10A:
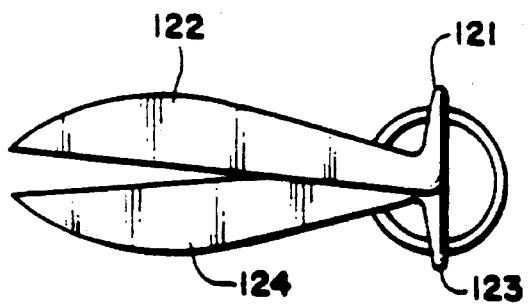
FIGS. 10 (a) to (c) illustrate an embodiment of the device of this invention in which the elements are splayed and in which the body portions of the elements are bent when the elements are unconstrained.
Figure 10B:
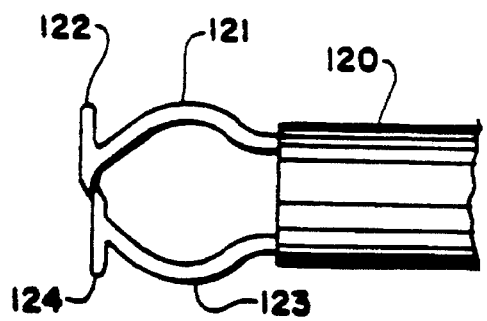
Figure 10C:
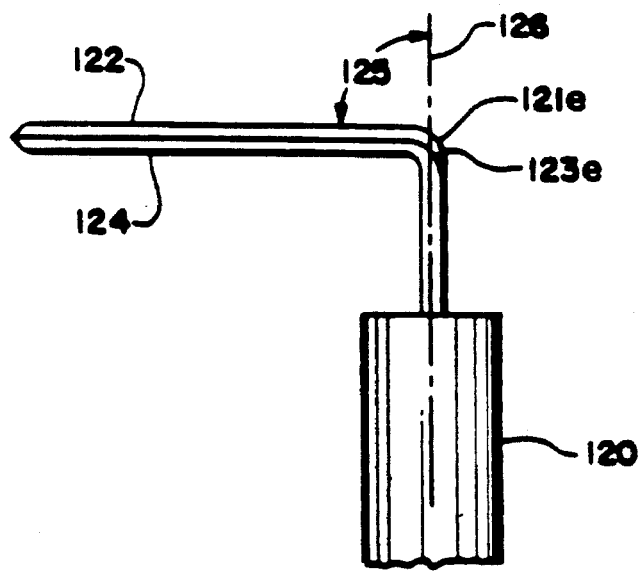

FIGS. 10 (a), (b), and (c) illustrate three views of another embodiment. As elongate elements 121 and 123 are extended outside the housing 120, they splay outward causing end portions 122 and 124 to separate also. When elongate elements 121 and 123 are partially withdrawn into housing 120, they cause end portions 122 and 124 to approach each other. If elongate elements 121 and 123 are further withdrawn into housing 120, the sections 121e and 123e of elongate elements 121 and 123 are forced to deform into straightened shapes in order to pass into housing 120, thus causing the direction of orientation of end portions 122 and 124 to approach the direction of axis 126 of housing 120, and the angle 125 approaches zero degrees (angle 125 is defined by axis 126 of housing 120 and the plane of end portions 122 and 124). End portions 122 and 124 may also be fully or partially withdrawn into housing 120, if desired. The straight configuration permits easy placement and/or removal of the instrument into or from a body in a compact and relatively atraumatic fashion. However, with elongate elements 121 and 123 in a completely extended position, angle 125 permits access to difficult to reach locations.

In the embodiments shown in FIGS. 10 (a), (b), and (c), the body portions of elongate elements 121 and 123 are preferably made of a pseudoelastic material and more preferably a superelastic shape memory alloy. Alternatively, sections 121e and 123e may be the only parts of elongate elements 121 and 123 which are made of a pseudoelastic material. End portions 122 and 124 may also be made of a pseudoelastic material, but they could be made of any suitable material, even if elements 121 and 123 are made at least in part of a pseudoelastic material. End portions 122 and 124 may have a cutting function or a grasping function. Also, end portions 122 and 124 may be curved. They may also be used to separate (dissect) tissues. The described mode of action may permit the instrument to be used multiple times in each location.

Figure 11A:
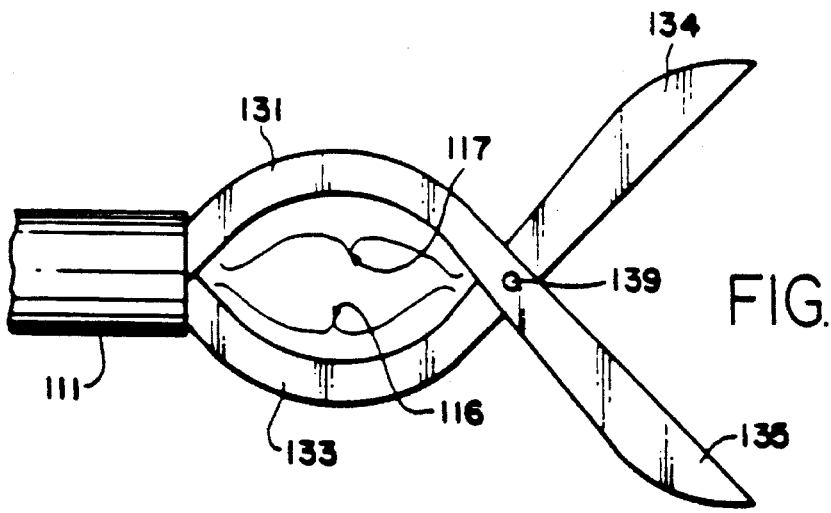
FIGS. 11 (a) and (b) illustrate a device of this invention in which the elements have end portions beyond a pivot point, and in which the body portions of the elements are of pseudoelastic material and when unconstrained are bent to splay the end portions and position them at a desired angle with respect to the hollow component. The body portions act as actuating means to open and close the end portions of the elements to dissect, grasp and/or cut an object.
Figure 11B:
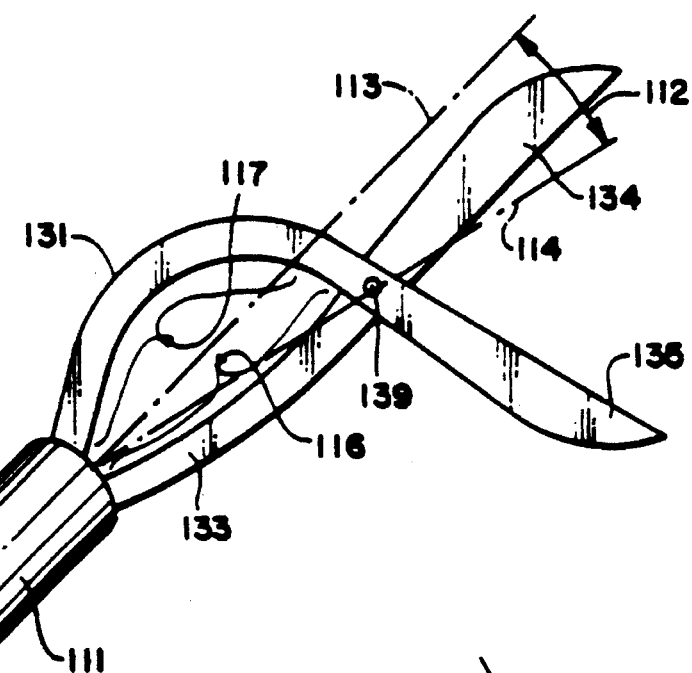

FIGS. 11 (*a*) and 11 (*b*) show embodiments similar to the embodiments shown in FIGS. 1 and 8, respectively. In FIGS. 11 (*a*) and 11(*b*), the elongate elements 131 and 133 extend beyond the pin 139 in order to provide end portions 135 and 134. End portions 135 and 134 may be unitary extensions of elongate elements 131 and 133 or they may be separate portions bolted or attached to elongate elements 131 and 133. The action of withdrawing elongate elements 131 and 133 into housing 111 closes and deforms body portions 117 and 116, and the scissor action is transmitted to end portions 135 and 134. In this manner, the body portions of the elongate elements act as the actuating means for the end portions of the elongate elements. FIG. 11 (*b*) illustrates a curved version of FIG. 11 (*a*). The angle 112 is defined by the axis 113 of housing 111 and the straight line 114 passing through the point of intersection of axis 113 with the distal end of the housing and pin 139. Angle 112 can be any number of degrees, even greater than 90 degrees, thus permitting dissection, cutting and/or grasping in a direction off axis 113. This provides access to difficult to reach locations within a body.

In the embodiments of FIGS. 11 (*a*) and 11 (*b*), body portions 116 and 117 are preferably made of a pseudoelastic material, preferably a superelastic shape memory alloy. Alternatively, only end portions 134 and 135 may be made of a pseudoelastic material, but these end portions could be made of any suitable material, even if body portions 116 and 117 are made of a pseudoelastic material. End portions 134 and 135 may have a cutting function or a grasping function. They may also be used to separate and dissect tissues. The described mode of action may permit the instrument to be used multiple times in each location.

Figure 12:
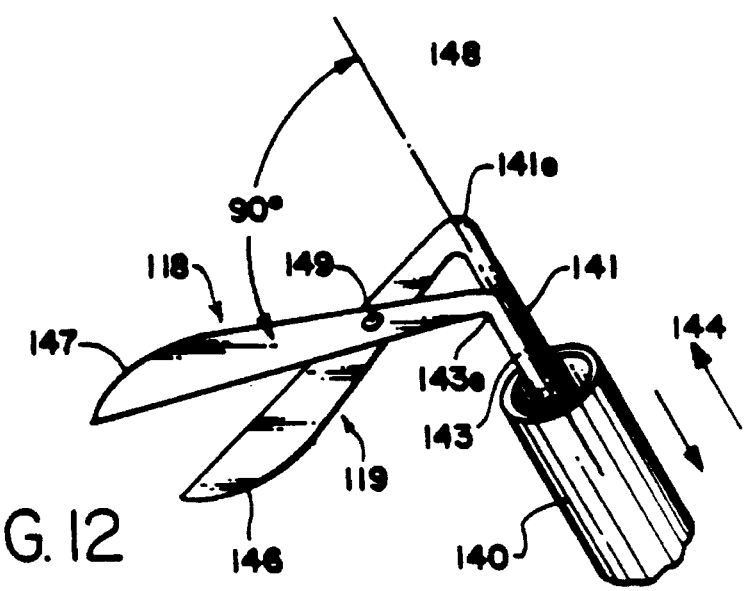
FIG. 12 illustrates a device similar to the device in FIG. 11(b), but in which the body portions of the elements are made of a pseudoelastic material and have a bend of about 90°.

FIG. 12 illustrates another embodiment similar to the embodiment shown in FIG. 11 (*b*). Body portions 141 and 143 of elongate elements 119 and 118 are used to create both a scissors action through a pinned location 149 and also to provide the ability to direct the scissor action at an angle of about ninety degrees off the axis 148 of housing 140. Elongate elements 119 and 118 splay apart when they are outside of housing 140. As housing 140 is pushed over the body portions 141 and 143 in direction 144, sections 141*e* and 143*e* move toward one another. This action in turn causes the end portions 146 and 147 to approach each other in a scissor fashion by pivoting around pin 149, which is substantially parallel to axis 148. Because the relative movement of housing 140 in directions 144 and 145 is perpendicular to end portions 146 and 147, the position of these end portions is unchanged with respect to the tissue location. After end portions 146 and 147 have closed, withdrawal of elongate elements 119 and 118 into housing 140 (or moving housing 140 in direction 144 relative to elongate elements 119 and 118) causes sections 141*e* and 143*e* to straighten from their curved shapes. This permits end portions 146 and 147 to generally align with axis 148 of housing 140. End portions 146 and 147 may also be fully or partially withdrawn into housing 140, if desired. The straight configuration permits easy placement and/or removal of the instrument from a body in a compact and relatively atraumatic fashion.

In the embodiments of FIG. 12, body portions 141 and 143 of elongate elements 119 and 118 are preferably made of a pseudoelastic material, more preferably a superelastic shape memory alloy. Alternatively, sections 141*e* and 143*e* may be the only parts of body portions 141 and 143 which are made of pseudoelastic material. End portions 146 and 147 may also be made of pseudoelastic material, but they could be made of any suitable material, even if body portions 141 and 143 are made at least in part of a pseudoelastic material. End portions 146 and 147 may have a cutting function or a grasping function. They may also be used to separate (dissect) tissues. The described mode of action may permit the instrument to be used multiple times in each location.

A variation of the embodiment shown in FIG. 12 would still have the bent portions 141*e* and 143*e*, but would have end portions 146 and 147 in a plane which is parallel to axis 148, so that pivot 149 is perpendicular to axis 148. In this embodiment, moving body portion 141 in direction 144 and/or moving body portion 143 in direction 145 would tend to splay end portions 146 and 147 apart. Moving body portion 141 in direction 145 and/or moving element 143 in direction 144 would tend to bring end portions 146 and 147 into a more overlapped configuration. In this manner, the body portions of the elongate elements act as the actuating means for the end portions of the elongate elements. In order to facilitate the requisite bending in sections 141*e* and 143*e*, body portions 141 and 143 would preferably be either round or made of flat material oriented in a plane perpendicular to the plane of end portions 146 and 147. If body portions 141 and 143 are made of flat material, they may include a 90 degree twist in the material between sections 141*e* and 143*e* and end portions 146 and 147, respectively.

Figure 13:
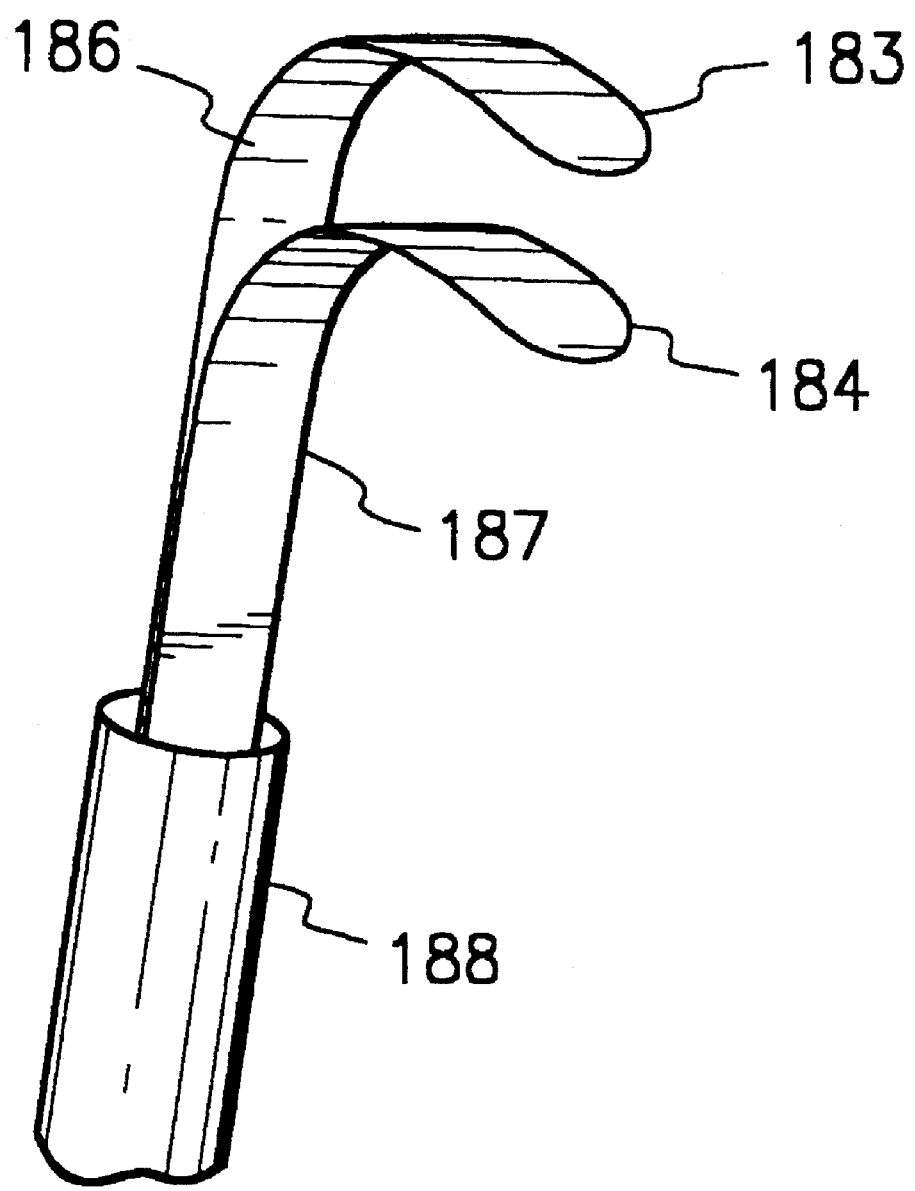
FIG. 13 illustrates another device in accordance with this invention.

FIG. 13 shows a device of this invention in which the elongate elements 186 and 187 are bent, preferably about 90 degrees, relative to the longitudinal axis of housing 188. The elongate elements are slid longitudinally along the axis of housing 188 by means of any suitable manually operated mechanism in order to separate end portions 183 and 184 from each other or to bring end portions 183 and 184 toward each other or even in contact with each other. End portions 183 and 184 can have any suitable surfaces in order to permit dissection, cutting, and/or grasping. Elongate elements 186 and 187 are preferably made of a pseudoelastic material, more preferably a superelastic shape memory alloy. This permits the bent portions of elongate elements 186 and 187 to be deformed and straightened so that the elongate elements can be withdrawn into housing 188. The straight configuration permits easy placement and/or removal of the instrument from a body in a compact and relatively atraumatic fashion. End portions 183 and 184 may be made of any suitable material, whether it is pseudoelastic or not.

In any of the embodiments of this invention, preferably both of the elongate elements are actuated by the manually operated mechanism, so that dissection, cutting, and/or grasping is done by an equal symmetrical motion of each elongate element. However, in some situations, it may be desirable to have embodiments in which one elongate element is moved more by the manually operated mechanism than the other elongate element. In some cases, it may even be desired to have one elongate element function as a stationary and thereby passive element, where the manually operated mechanism only moves the other elongate element.

In any of the embodiments of this invention, any suitable manually operated mechanism may be utilized to move the elongate elements. Possible mechanisms include sliders, pistol grip handles, scissors handles, and syringe-plunger arrangements. In any of the embodiments of this invention, it may be desirable to be able to axial rotate the elongate elements relative to the manually operated mechanism, so that the elongate elements can be pointed in a preferred direction without having to rotate the manually operated mechanism itself. This feature would enhance the comfort of using a device of this invention. However, a means is preferably provided to prevent any undesired axial rotation of the elongate elements relative to the manually operated mechanism while the manually operated mechanism is being used to splay or overlap the elongate elements.

In any of the embodiments of this invention, a suitable means may be provided for passing a fluid (liquid or gas) through the device for irrigation, aspiration, insufflation, etc. In any of the embodiments of this invention, electricity may be passed to one or both end portion(s) of the elongate element(s) for purposes of electrocautery or electrocutting.

In any of the embodiments of this invention, the tips (of the end portions) of the elongate elements may be pointed or blunt. Pointed tips may facilitate the use of the device of this invention in the separation (dissection) of tissues, while blunt tips would minimize the risk of any undesired trauma that the tips could inflict upon tissues.

While the invention has been described in connection with specific embodiments thereof, those skilled in the art will recognize that various modifications are possible within the principles described herein. Such modifications, variations, uses, or adaptations of the invention, including such departures from the present disclosure as come within known or customary practice in the art, fall within the scope of the invention and of the appended claims.

What is claimed is:

1. A device for dissecting an object which comprises at least two elongate elements, positioned alongside one another, each having a body portion and an end portion, the end portions of the elements including means for:
   i. being capable of being splayed apart from one another when free of transverse constraint to dissect said object from surrounding material; and
   ii. being capable of being moved toward one another; wherein a portion of at least one of the elements is formed from a pseudoelastic material.

2. A device for manipulating an object which comprises at least two elongate elements, positioned alongside one another, each having a body portion and an end portion, the end portions of the elements including means for:
   i. being capable of being splayed apart from one another when free of transverse constraint and presenting manipulating surfaces to an object to be manipulated that is placed between them; and
   ii. being capable of being moved toward one another to manipulate said object;
wherein a portion of at least one of the elements is formed from a pseudoelastic material.

3. A device for dissecting an object which comprises
   a. a hollow elongate component; and
   b. at least two elongate elements, at least part of which are positioned within said component, said elements being positioned alongside one another, each having a body portion and an end portion, the end portions of the elements including means for:
      i. being capable of being splayed apart from one another when free of transverse constraint to dissect said object from surrounding material; and
      ii. being capable of being moved toward one another;
wherein the elements and the component are longitudinally slideable relative to one another so that at least a portion of the elements can be slide into and out of said component and wherein a portion of at least one of the elements is formed from a pseudoelastic material.

4. A device for manipulating an object which comprises
   a. a hollow elongate component; and
   b. at least two elongate elements, at least part of which are positioned within said component, said elements being positioned alongside one another, each having a body portion and an end portion, the end portions of the elements including means for:
      i. being capable of being splayed apart from one another when free of transverse constraint and presenting manipulating surfaces to an object to be manipulated that is placed between them; and
      ii. being capable of being moved towards one another to manipulate said object;
wherein the elements and the component are longitudinally slideable relative to one another so that at least a portion of the elements can be slid into and out of said component and wherein a portion of at least one of the elements is formed from a pseudoelastic material.

5. A device as claimed in claim 1, 2, 3, or 4, wherein the pseudoelastic material is a pseudoelastic shape memory alloy.

6. A device as claimed in claim 1, 2, 3, or 4, wherein the pseudoelastic material is a superelastic material.

7. A device as claimed in claim 1, claim 2, claim 3, or claim 4, in which the end portions of the elements are pivotally connected to one another towards their free ends.

8. A device as claimed in claim 1, 2, 3 or 4 wherein the end portions of the elements are pivotally connected to one another.

9. A device as claimed in claim 2 or 4 wherein the means for manipulating comprises means for cutting said object.

10. A device as claimed in claim 2 or 4 which further comprises a cutting edge of a material other than a shape memory alloy.

11. A device for manipulating an object which comprises at least two elongate elements positioned alongside one another, each having a body portion and an end portion, at least a portion of at least one of the elongate elements including a manipulating edge constructed of a material other than a shape memory alloy, the end portions of the elements including means for:
   i. being capable of being splayed apart from one another when free of transverse constraint and presenting manipulating surfaces to an object to be manipulated that is placed between them; and
   ii. being capable of being moved toward one another to manipulate said object;
wherein a portion of at least one of the elements is formed from a pseudoelastic material.

12. A device as claimed in claim 11, wherein said cutting edge is of stainless steel.

13. A device as claimed in claim 2, or claim 4, which further comprises at least one grasping surface.

14. A method of manipulating an object, which comprises:
   A. providing a device which comprises
      a. at least two elongate elements, positioned alongside one another, each having a body portion and an end portion, the end portions of the elements:
         i. being capable of being splayed apart from one another when free of transverse constraint and presenting manipulating surfaces to an object to be manipulated that is placed between them; and ii. being capable of being moved toward one another to manipulate said object;

wherein at least a portion of at least one of the elements is formed from a pseudoelastic material;

B. positioning the object between the splayed apart end portions of the elements; and C. causing said end portions to move toward one another so as to manipulate said object.

15. A method of manipulating an object, which comprises:

A. providing a device which comprises:

a. a hollow elongate component; and b. at least two elongate elements, at least part of which are positioned within said component, said elements being positioned alongside one another, each having a body portion and an end portion, the end portions of the elements:

i. being capable of being splayed apart from one another when free of transverse constraint and presenting manipulating surfaces to an object to be manipulated that is placed between them; and ii. being capable of being moved toward one another to manipulate said object;

wherein the elements and the component are longitudinally slideable relative to one another so that at least a portion of the elements can be slid into and out of said component and wherein at least a portion of at least one of the elements is formed from a pseudoelastic material;

B. positioning said object between the splayed apart end portions of the elements; and C. causing said end portions to move toward one another so as to manipulate said object.

16. A method of claim 14, or 15, wherein the pseudoelastic material is a superelastic material.

17. A method as claimed in claim 16, wherein the pseudoelastic material is a shape memory alloy.

18. A method of dissecting an object from surrounding material as claimed in claim 16 wherein the shape memory alloy is a nickel titanium alloy.

19. A method as claimed in claim 14, or claim 15, in which the object is a part of a human body or animal body.

20. A method as claimed in claim 19, in which the object is an internal part of the body, and the method includes the step of positioning at least the end portions of the elements within the body.

21. A method as claimed in claim 14 or 15 wherein the step of manipulating said object comprises cutting said object.

* * * * *